(12) United States Patent
Li et al.

(10) Patent No.: US 12,208,282 B2
(45) Date of Patent: Jan. 28, 2025

(54) CAVITY OF MEDICAL DEVICE AND MEDICAL SYSTEM INCLUDING THE MEDICAL DEVICE

(71) Applicant: SHANGHAI UNITED IMAGING HEALTHCARE CO., LTD., Shanghai (CN)

(72) Inventors: Xiaobin Li, Shanghai (CN); Jianning Zhang, Shanghai (CN); Yifeng Wang, Shanghai (CN); Jian Zhang, Shanghai (CN); Wei Qi, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 224 days.

(21) Appl. No.: 17/930,059

(22) Filed: Sep. 6, 2022

(65) Prior Publication Data

US 2023/0070469 A1 Mar. 9, 2023

(30) Foreign Application Priority Data

Sep. 6, 2021 (CN) .......................... 202111038952.9

(51) Int. Cl.
*A61N 5/10* (2006.01)
(52) U.S. Cl.
CPC ........ *A61N 5/10* (2013.01); *A61N 2005/1055* (2013.01)
(58) Field of Classification Search
CPC .......................... A61N 5/10; A61N 2005/1055
See application file for complete search history.

(56) References Cited

U.S. PATENT DOCUMENTS

| | | | |
|---|---|---|---|
| 5,097,131 A | 3/1992 | Plummer et al. | |
| 2007/0242801 A1* | 10/2007 | Mackie | A61N 5/1042 378/65 |
| 2008/0267358 A1* | 10/2008 | Hiyama | A61B 6/04 378/209 |
| 2011/0012593 A1* | 1/2011 | Shvartsman | G01R 33/3806 324/307 |
| 2013/0208866 A1* | 8/2013 | Bergfjord | A61B 6/0407 378/65 |
| 2014/0128719 A1* | 5/2014 | Longfield | G01R 33/3815 600/411 |
| 2018/0133508 A1* | 5/2018 | Pearce | A61N 5/107 |
| 2018/0133518 A1* | 5/2018 | Harper | A61N 5/1049 |
| 2018/0164392 A1* | 6/2018 | George | A61B 5/055 |
| 2019/0030366 A1* | 1/2019 | Maltz | A61B 5/0536 |
| 2019/0143145 A1* | 5/2019 | Laurence, Jr. | A61N 5/1081 600/1 |
| 2021/0106252 A1* | 4/2021 | Shinkai | A61B 5/055 |
| 2022/0305292 A1* | 9/2022 | Harper | A61N 5/1081 |

* cited by examiner

*Primary Examiner* — Hugh Maupin
(74) *Attorney, Agent, or Firm* — METIS IP LLC

(57) ABSTRACT

The present disclosure relates to a cavity of a medical device. The cavity may include a bore and an accommodating cavity configured to provide an accommodating space for at least a portion of a couch in a radial direction of the bore. The accommodating cavity may be disposed on an inner wall of the bore and extend along an axial direction of the bore, and the accommodating cavity may be configured to form, with the bore, a connected space in which the at least a portion of the couch is allowed to move along an axial direction of the bore.

20 Claims, 11 Drawing Sheets

CAVITY OF MEDICAL DEVICE AND MEDICAL SYSTEM INCLUDING THE MEDICAL DEVICE

CROSS-REFERENCE TO RELATED APPLICATIONS

This application claims priority of Chinese Patent Application No. 202111038952.9, filed on Sep. 6, 2021, the contents of which are incorporated herein by reference.

TECHNICAL FIELD

The present disclosure generally relates to a medical device, and more particularly, to a cavity of a medical device and a system including the medical device.

BACKGROUND

Medical devices, such as imaging devices and treatment devices, are used separately or in combination for imaging and/or treatment. A medical device usually includes a bore configured to accommodate a patient and a couch configured to support the patient and move into or out of the bore. The bore of the medical device typically has a standard circular cross-section. When the couch moves into the bore, a movement range in a vertical direction of the couch may be limited by an inner wall of the bore, which results in limited imaging or treatment space, and increases the difficulty of adjusting the patient's position. As a result, an imaging or treatment procedure becomes more complicated, which reduces the imaging or treatment efficiency and even affects the execution of the treatment.

Therefore, it is desirable to provide a medical device with an improved cavity.

SUMMARY

An aspect of the present disclosure relates to cavity of a medical device. The cavity may include a bore and an accommodating cavity configured to provide an accommodating space for at least a portion of a couch in a radial direction of the bore. The accommodating cavity may be disposed on an inner wall of the bore and extends along an axial direction of the bore, and the accommodating cavity may be configured to form, with the bore, a connected space in which the at least a portion of the couch is allowed to move along an axial direction of the bore.

In some embodiments, a length of the accommodating cavity may be less than a length of the bore in the axial direction.

In some embodiments, the accommodating cavity may extend from an entrance of the bore.

In some embodiments, the accommodating cavity may be configured to accommodate a couch top of the couch. A width of the accommodating cavity may be larger than a width of the couch top.

In some embodiments, the couch may include a support portion configured to support the couch top, and the accommodating cavity may be configured to accommodate the support portion. A width of the accommodating cavity may be larger than a width of the support portion.

In some embodiments, the accommodating cavity may be configured to accommodate the at least a portion of the couch in a vertical direction.

In some embodiments, a cross section of the cavity may be of a shape other than a circle.

In some embodiments, the cross section of the cavity may be polygonal.

In some embodiments, a movement range of the at least a portion of the couch in a first direction may be larger than a movement range of the at least a portion of the couch in a second direction. The first direction and the second direction may be radial directions of the bore, and an included angle between the first direction and the second direction may be larger than 0. In some embodiments, the first direction may be a vertical direction.

In some embodiments, a distance between a center line of the bore in the axial direction and an upper inner wall of the cavity may be less than a distance between the center line and a lower inner wall of the cavity.

In some embodiments, the cavity may further include an adjustment assembly including a raised configuration and a retracted configuration. When the adjustment assembly is at the retracted configuration, a distance between the adjustment assembly and an opening of the accommodating cavity may be larger than 0.

In some embodiments, the adjustment assembly may include a cover configured to cover the opening of the accommodating cavity when the adjustment assembly is at the raised configuration.

In some embodiments, the cavity may further include a control assembly configured to control the adjustment assembly to switch between the raised configuration and the retracted configuration.

In some embodiments, the cavity may further include a second accommodating cavity. The second accommodating cavity may be configured to form, with the bore and the accommodating cavity, the connected space.

Another aspect of the present disclosure relates to a system. The system may include a first medical device and a second medical device. A first bore of the first medical device and a second bore of the second medical device may be coaxial and connected with each other. The system may further include a couch including a couch top configured to move into or out of the first bore and the second bore along an axial direction. The first medical device or the second medical device may include an accommodating cavity that forms, with the first bore or the second bore, a connected space. The accommodating cavity may be configured to provide an accommodating space for at least a portion of the couch in a radial direction of the first bore or the second bore.

In some embodiments, the second medical device may be disposed between the first medical device and the couch, and the second medical device may include the accommodating cavity.

In some embodiments, the accommodating cavity may be disposed on an inner wall of the second bore and extends from an entrance of the second bore along the axial direction. A length of the accommodating cavity may be less than a length of the second bore in the axial direction.

In some embodiments, the accommodating cavity may be configured to accommodate a support portion of the couch that is configured to support the couch top to allow the support portion to move in at least one of the first bore or the second bore along the axial direction.

In some embodiments, the first medical device may include an imaging device, and the second medical device may include a radiation therapy device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
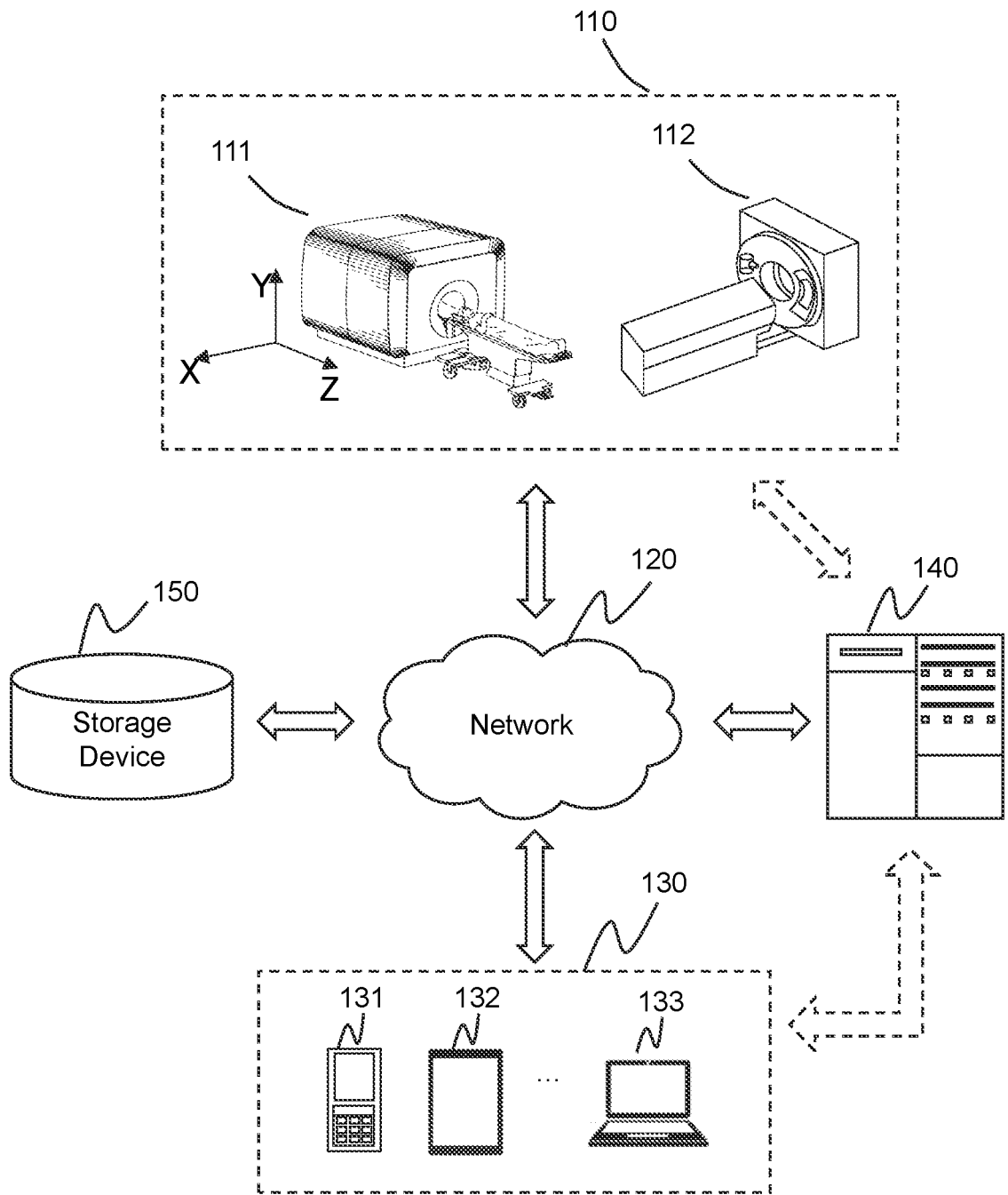
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this disclosure, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections, or assemblies of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules (or units or blocks) may be included in connected logic components, such as gates and flip-flops, and/or can be included in programmable units, such as programmable gate arrays or processors. The modules (or units or blocks) or computing device functionality described herein may be implemented as software modules (or units or blocks), but may be represented in hardware or firmware. In general, the modules (or units or blocks) described herein refer to logical modules (or units or blocks) that may be combined with other modules (or units or blocks) or divided into sub-modules (or sub-units or sub-blocks) despite their physical organization or storage.

It will be understood that when a unit, engine, module, or block is referred to as being "on," "connected to," or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only and is not intended to be limiting. As used herein, the singular forms "a," "an," and "the" may be intended to include the plural forms as well, unless the context clearly indicates otherwise. It will be further understood that the terms "include" and/or "comprise," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Spatial and functional relationships between elements are described using various terms, including "connected," "engaged," "interfaced," and "coupled." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. In addition, a spatial and functional relationship between elements may be achieved in various ways. For example, a mechanical connection between two elements may include a welded connection, a key connection, a pin connection, an interference fit connection, or the like, or any combination thereof. Other words used to describe the relationship between elements should be interpreted in a like fashion (e.g., "between," versus "directly between," "adjacent," versus "directly adjacent," etc.).

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure may provide a cavity of a medical device and a system including the medical device. The cavity may include a bore and an accommodating cavity. The accommodating cavity may be disposed on an inner wall of the bore and extend along an axial direction of the bore. And the accommodating cavity may be configured to form, with the bore, a connected space in which at least a portion of a couch is allowed to move along an axial direction of the bore. In some embodiments, the accommodating cavity may be configured to accommodate a couch top and/or a support portion of the couch.

According to the cavity provided in the present disclosure, the accommodating cavity may be provided for accommodating at least a portion of the couch. In such cases, a movement range of the at least a portion of the couch in the medical device may be increased, which may reduce the difficulty of adjusting a position of a subject (e.g., a patient) during an imaging procedure, thereby improving the accuracy of imaging and/or treatment of a target region of the subject and further improving the treatment efficiency. Furthermore, the accommodating cavity may be obtained by modifying a bore of a traditional medical device. And a position of the accommodating cavity may not interfere with other components (e.g., imaging components, treatment components, etc.) of the medical device. That is, the medical device of the present disclosure may be obtained without any changes to other components of a traditional medical device, which may simplify the manufacturing process of the medical device. Moreover, a size (e.g., a volume) of the medical device of the present disclosure may remain (substantially) the same as a size of the traditional medical device, and accordingly a space occupied by or needed to house the medical device may remain (substantially) the same as a space occupied by or needed to house the traditional medical device.

FIG. 1 is a schematic diagram illustrating an exemplary medical system according to some embodiments of the present disclosure. As illustrated, the medical system 100 may include a medical device 110, a network 120, a terminal device 130, a processing device 140, and a storage device 150. The components of the medical system 100 may be connected in one or more of various ways. For example, the medical device 110 may be connected to the processing device 140 through the network 120. As another example, the medical device 110 may be connected to the processing device 140 directly (as indicated by the bi-directional arrow in dotted lines linking the medical device 110 and the processing device 140). As a further example, the storage device 150 may be connected to the processing device 140 directly or through the network 120. As still a further example, the terminal device 130 may be connected to the processing device 140 directly (as indicated by the bi-directional arrow in dotted lines linking the terminal device 130 and the processing device 140) or through the network 120.

The medical device 110 may include any device used in a medical procedure. As used herein, a medical procedure may refer to an activity or a series of actions taken to achieve a result in the delivery of healthcare, for example, directed at or performed on a subject (e.g., a patient) to measure, diagnose, and/or treat the subject. Exemplary medical procedures may include a diagnostic procedure (e.g., an imaging procedure), a treatment procedure (e.g., a radiotherapy treatment procedure), etc. The subject may be biological or non-biological. For example, the subject may include a patient, a man-made object, etc. As another example, the subject may include a specific portion, an organ, and/or tissue of the patient. For example, the subject may include the head, the neck, the thorax, the heart, the stomach, blood vessels, soft tissues, tumors, nodules, or the like, or a combination thereof.

In some embodiments, the medical device 110 may include an imaging device, a treatment device (e.g., a radiotherapy apparatus), a multi-modality device to acquire one or more images of different modalities or acquire an image relating to at least one part of a subject and perform treatment on the at least one part of the subject, etc. The imaging device may be configured to generate an image including a representation of at least one part of the subject. Exemplary imaging devices may include, for example, a computed tomography (CT) device, a cone beam CT device, a positron emission computed tomography (PET) device, a volume CT device, a magnetic resonance imaging (MRI) device, or the like, or a combination thereof. The treatment device may be configured to perform a treatment on at least one part of the subject. Exemplary treatment devices may include an X-ray treatment device, a radiation therapy (RT) device, etc.

The network 120 may include any suitable network that can facilitate the exchange of information and/or data for the medical system 100. In some embodiments, one or more components (e.g., the medical device 110, the terminal device 130, the processing device 140, the storage device 150) of the medical system 100 may communicate with one or more other components of the medical system 100 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. In some embodiments, the network 120 may include one or more network access points. For example, the network 120 may include wired and/or wireless network access points such as base stations and/or internet exchange points through which one or more components of the medical system 100 may be connected to the network 120 to exchange data and/or information.

The terminal device 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the medical device 110 and/or the processing device 140 may be remotely operated through the terminal device 130. In some embodiments, the medical device 110 and/or the processing device 140 may be operated through the terminal device 130 via a wireless connection. In some embodiments, the terminal device 130 may receive information and/or instructions inputted by a user, and send the received information and/or instructions to the medical device 110 or the processing device 140 via the network 120. In some embodiments, the terminal device 130 may receive data and/or information from the processing device 140. In some embodiments, the terminal device 130 may be part of the processing device 140. In some embodiments, the terminal device 130 may be omitted.

The processing device 140 may process data and/or information obtained from the medical device 110, the terminal device 130, the storage device 150, and/or any other components associated with the medical system 100. For example, the medical device 110 may include an imaging device 111 and a radiation therapy device 112. The processing device 140 may determine treatment parameters of the radiation therapy device based on imaging data collected or generated by the imaging device 111. Exemplary treatment parameters may include, but are not limited to, a radiation dose, a rotation angle of a treatment head, etc. As another example, the processing device 140 may obtain user instructions from the terminal device 130. As a further example, the processing device 140 may transmit control instructions to one or more components (e.g., the medical device 110, a couch) of the medical system 100. For instance, the processing device 140 may transmit control instructions to the medical device 110 to control moveable components (e.g., an ionization chamber, a detector, a drum, etc.) to move to desired positions. For another instance, the processing device 140 may transmit a control instruction to the terminal device 130 to display image data on an interface of the terminal device 130. For a further instance, the processing device 140 may transmit instructions to cause a couch of the medical device 110 to move into or out of a bore of the medical device 110. In some embodiments, the processing device 140 may be a single server or a server group. The server group may be centralized or distributed. In some embodiments, the processing device 140 may be local or remote. For example, the processing device 140 may access information and/or data stored in or acquired by the medical device 110, the terminal device 130, the storage device 150, and/or any other components associated with the medical system 100 via the network 120. As another example, the processing device 140 may be directly connected to the medical device 110 (as illustrated by the bidirectional arrow in dashed lines connecting the processing device 140 and the medical device 110 in FIG. 1), the terminal device 130 (as illustrated by the bidirectional arrow in dashed lines connecting the processing device 140 and the terminal device 130 in FIG. 1), and/or the storage device 150 to access stored or acquired information and/or data. In some embodiments, the processing device 140 may be part of the medical device 110. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 150 may store data and/or instructions. In some embodiments, the storage device 150 may store data obtained from the medical device 110, the terminal device 130, and/or the processing device 140. For example, the storage device 150 may store scan data of a subject acquired by the medical device 110. In some embodiments, the storage device 150 may store data and/or instructions that the processing device 140 may execute or use to perform exemplary methods described in the present disclosure. For example, the storage device 150 may store instructions that the processing device 140 may execute to control the medical device. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components (e.g., the medical device 110, the processing device 140, the terminal device 130) of the medical system 100. One or more components of the medical system 100 may access the data or instructions stored in the storage device 150 via the network 120. In some embodiments, the storage device 150 may be part of the processing device 140.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 2:
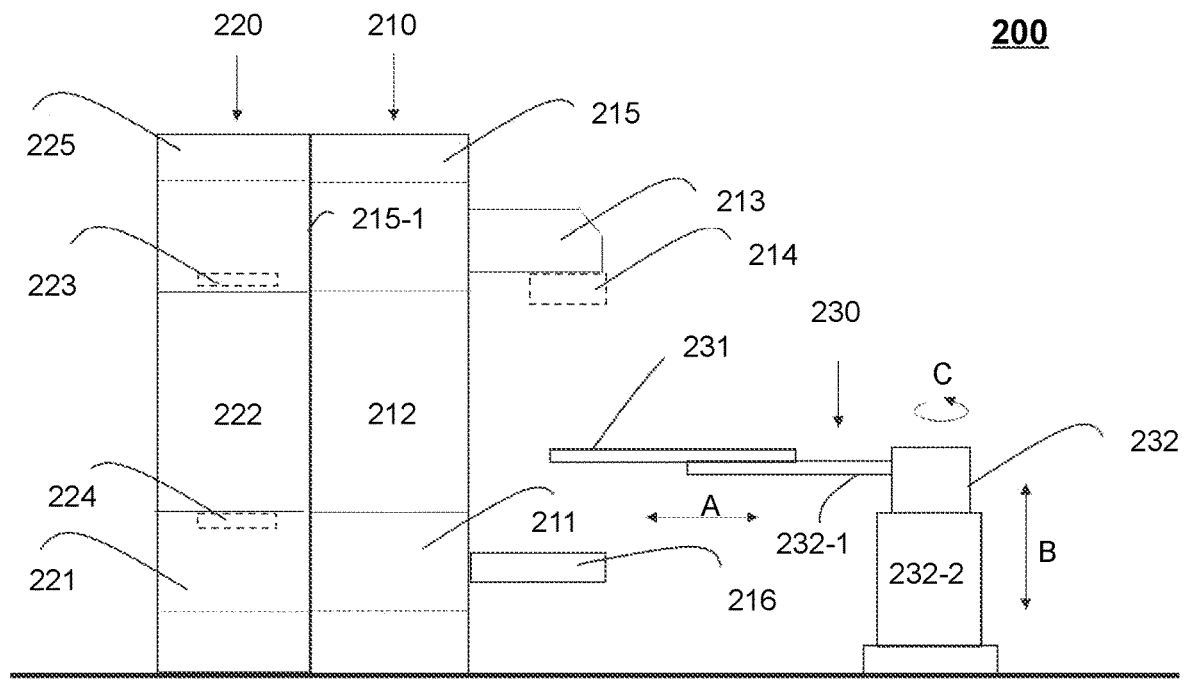
FIG. 2 is a schematic diagram illustrating an exemplary medical system according to some embodiments of the present disclosure.

FIG. 2 is a schematic diagram illustrating an exemplary medical system according to some embodiments of the present disclosure. In some embodiments, the medical system 200 may be a radiotherapy system. As illustrated in FIG. 2, the medical system 200 may include a radiation therapy device 210, an imaging device 220, and a couch 230.

The radiation therapy device 210 may be configured to apply a treatment on at least a portion of a subject (e.g., a patient). The radiation therapy device 210 may include a drum 211 that defines a bore 212. The bore 212 may extend in the horizontal direction A. An axial direction of the bore 212 may be parallel to the horizontal direction A. The bore 212 may be configured to accommodate the couch 230. The radiation therapy device 210 may also include treatment components such as a treatment arm 213, a treatment head 214, and an electronic portal imaging device 216. One end of the treatment arm 213 may be fixed to an outer wall of the drum 211, and the other end may extend outward away from the bore 212. The treatment head 214 may be fixed to the other end of the treatment arm 213 that is away from the bore 212. The electronic portal imaging device 216 may be disposed on the same outer wall of the drum 211 on which the treatment arm 213 is disposed. In some embodiments, the electronic portal imaging device 216 and the treatment head 214 may be symmetrical about an axis of the bore 212. The treatment head 214 may include a radiation source that is configured to emit a radiation beam towards a treatment region of the radiation therapy device 210. The radiation beam may include an X-ray beam, an electron beam, a gamma ray source, a proton ray source, etc. The electronic portal imaging device 216 may be used in conjunction with the treatment head 214 to adjust the radiation beam or a position of the subject. In some embodiments, the drum 211 may rotate around a rotation axis that is parallel to the horizontal direction. Correspondingly, the treatment head 214 may rotate, within a rotation plane, around the rotation axis. A center point of the rotation plane may be referred to as an isocenter of the radiation therapy device 210. A plane perpendicular to a central axis of the radiation beam emitted by the treatment head 214 and passing through the isocenter may be referred to as an isocenter plane.

In some embodiments, the radiation therapy device 210 may be a ring-shaped radiation therapy device. In the ring-shaped radiation therapy device, the treatment arm 213 may be omitted, and the treatment head 214 and the electronic portal imaging device 216 may be disposed in the drum 211. In some embodiments, the radiation therapy device 210 may include a housing 215. The housing 215 may be configured as a support portion for supporting the radiation therapy device 210.

The imaging device 220 may be configured to scan the subject and generate imaging data. The imaging device 220 may include a drum 221 that defines a bore 222. The bore 222 may extend in the horizontal direction A. In some embodiments, an axial direction of the bore 222 may be parallel to the horizontal direction A. The bore 222 may be configured to accommodate the couch 230. The imaging device 220 may also include imaging components such as a ray tube 223 and a detector 224. The ray tube 223 and the detector 224 may be disposed on an outer wall of the drum 221 and symmetrically about an axis of the bore 222. The drum 221, together with the ray tube 223 and the detector 224 mounted thereon, may rotate around a rotation axis parallel to the horizontal direction. The ray tube 223 may be configured to emit a radiation beam towards a scanning region of the imaging device 220. The detector 224 may be configured to detect a radiation beam impinging on the detector 224 and generate electrical signals for imaging. The imaging device 220 may include a housing 225. The housing 225 may be configured as a support portion for supporting the imaging device 220. In some embodiments, the imaging device 220 may include a CT device, an MR device, a PET device, etc.

The couch 230 may be configured to support the subject and/or carry the subject in or out of the bore 212 and/or the bore 222. The couch 230 may include a couch top 231 and a support component 232. The support component 232 may include a support portion 232-1 and a pedestal 232-2. The support portion 232-1 may be configured to support the couch top 231. And the pedestal 232-2 may be configured to support the support portion 232-1. The support component 232, including the support portion 232-1 and the pedestal 232-2, may be configured to adjust a position of the couch top 231, thereby adjusting a position of the subject or a portion thereof. For example, the couch top 231 may be caused to move along the horizontal direction A (or the axial direction of the bore 212 and/or the bore 222) to move into or out of the bore 212 and/or the bore 222. As another example, the couch top 231 may be caused to move along the vertical direction B to adjust a height of the subject in the bore 212 and/or the bore 222. As a further example, the couch top 231 may be caused to rotate along a circumferential direction C of the pedestal 232-2 to adjust the position of the subject in a horizontal plane parallel to the horizontal direction A.

In some embodiments, as shown in FIG. 2, the radiation therapy device 210 and the imaging device 220 may be connected to each other. For example, the radiation therapy device 210 may be operably connected to the imaging device 220 on the outer wall 215-1 of the housing 215. The bore 212 of the radiation therapy device 210 and the bore 222 of the imaging device 220 may be coaxial and operably connected with each other. The imaging device 220, the radiation therapy device 210, and at least a portion of the couch 230 (e.g., the pedestal 232-2 of the couch 230) may be placed in sequence along the horizontal direction A. In some embodiments, a shape and/or a size of a cross section of the bore 212 may be the same as a shape and/or a size of a cross section of the bore 222. In such cases, a projection of the bore 212 along the horizontal direction A may coincide with a projection of the bore 222 along the horizontal direction A.

Figure 3:
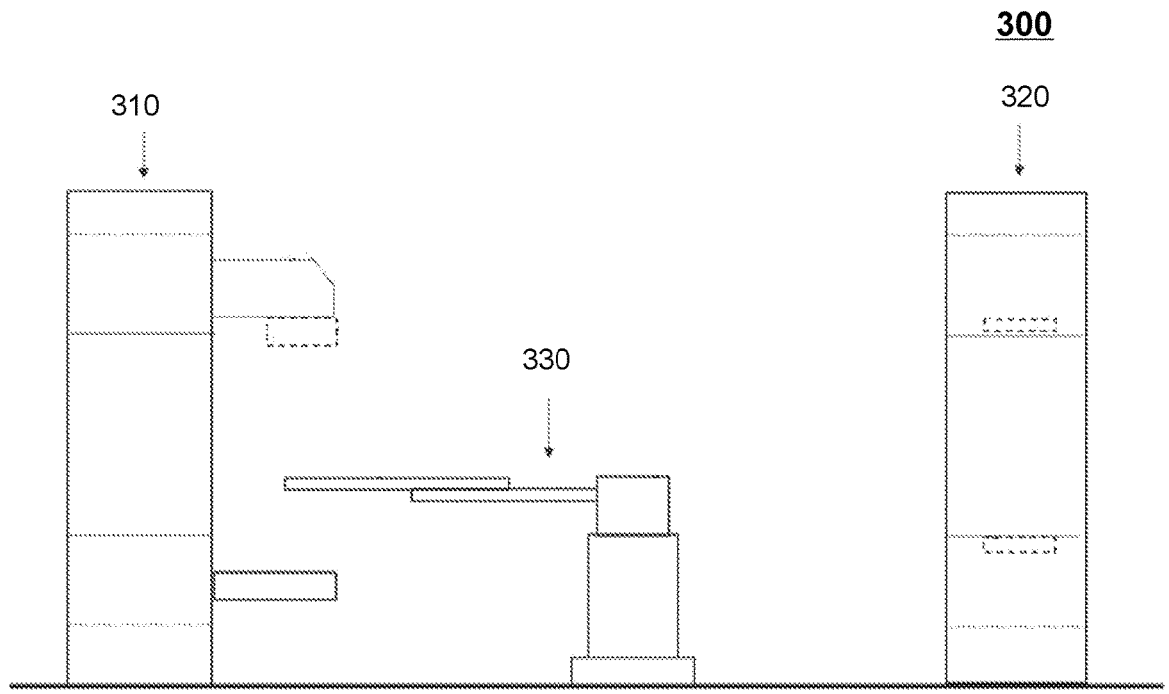
FIG. 3 is a schematic diagram illustrating another exemplary medical system according to some embodiments of the present disclosure.

FIG. 3 is a schematic diagram illustrating another exemplary medical system according to some embodiments of the present disclosure. In some embodiments, the medical system 300 may be a radiotherapy system. As illustrated in FIG. 3, the medical system 300 may include a radiation therapy device 310, an imaging device 320, and a couch 330. The medical system 300 illustrated in FIG. 3 may be similar to the medical system 200 illustrated in FIG. 2 except for a difference in relative positions of the radiation therapy device, the imaging device, and the couch. For example, as shown in FIG. 3, the radiation therapy device 310 and the imaging device 320 may be placed separately; at least a portion of the couch 330 (e.g., the pedestal 232-2) may be placed between the radiation therapy device 310 and the imaging device 320.

In some embodiments, the imaging device and the radiation therapy device of the medical system may be used separately or in combination for imaging and/or treatment. Taking the medical system 200 as an example, in an imaging procedure, a patient may be placed on the couch top 231 and the couch 230 may be controlled to position a region of interest (ROI) of the patient in a scanning region between the ray tube 223 and the detector 224. For example, the patient may be positioned such that the ROI is located on an isocenter plane of the imaging device 220 and/or a center of the ROI is aligned with (e.g., coincident with) the isocenter of the imaging device 220. Then the ROI may be scanned by a radiation beam emitted by the ray tube 223 and imaging data related to the ROI may be obtained. A target region of the patient to be treated may be determined based on the imaging data. Further, in a treatment procedure, the couch 230 may be controlled to position the target region of the patient at a treatment region between the treatment head 214 and the electronic portal imaging device 216 of the radiation therapy device 210. For example, the patient may be positioned such that the target region is located on the isocenter plane of the radiation therapy device 210 and/or a center of the target region is aligned with (e.g., coincident with) the isocenter of the radiation therapy device 210. Then the target region of the patient may be irradiated by a radiation beam emitted by the treatment head 214.

Figure 4:
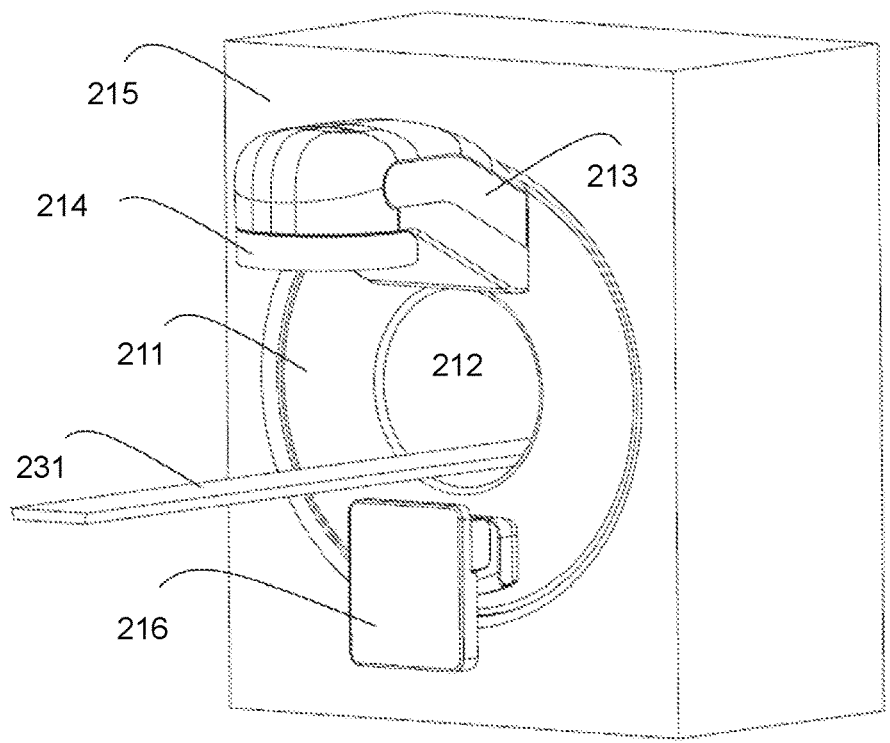
FIG. 4 is a schematic diagram illustrating an exemplary radiation therapy device illustrated in FIG. 2.
Figure 5:
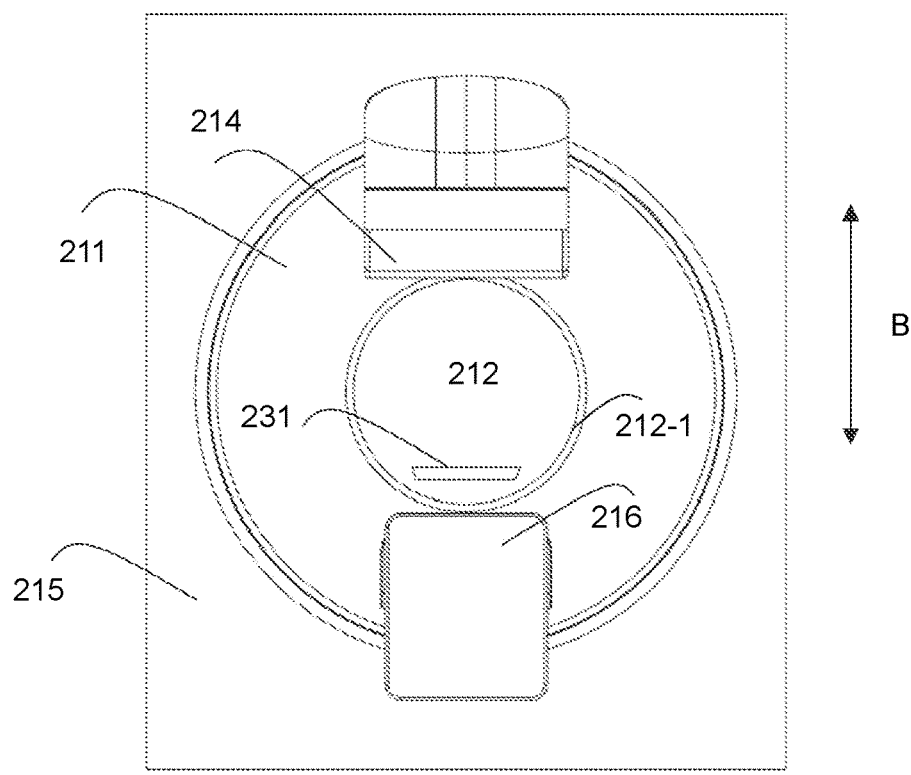
FIG. 5 is a schematic diagram illustrating a front view of the radiation therapy device illustrated in FIG. 4.

In some embodiments, a cross section of the bore (e.g., the bore 212, the bore 222, etc.) of the imaging device or the radiation therapy device may be circular, which may limit a movement range of a least a portion of the couch. Taking the radiation therapy device 210 as an example, FIG. 4 is a schematic diagram illustrating an exemplary radiation therapy device 210 illustrated in FIG. 2. FIG. 5 is a schematic diagram illustrating a front view of the radiation therapy device illustrated in FIG. 4. As shown in FIG. 4 and FIG. 5, the couch top 231 of the couch 230 may be raised or lowered in the bore 212 along the vertical direction B. A cross section of the bore 212 may be circular, and a movement range of the couch top 231 in the vertical direction B (e.g., a height that the couch top 231 can reach) may be limited by an inner wall 212-1 of the bore 212.

Moreover, in the medical system 200 illustrated in FIG. 2, in the imaging procedure, the subject may be placed on the couch top 231, the support portion 232-1 may move into the bore 212 of the radiation therapy device 210 to allow the couch top 231 to move into the bore 222 of the imaging device 220. As shown in FIG. 2, the support portion 232-1 may be disposed below the couch top 231, which may limit the movement range of the couch top 231 in the vertical direction B. For example, when the position of the subject needs to be lowered, the support portion 232-1 may descend to drive the couch top 231 down. Since the support portion 232-1 is disposed below the couch top 231, the support portion 232-1 may collide into the inner wall 212-1 of the bore 212, and the couch top 231 can not descend further. In such cases, the movement range (e.g., a descending height) of the couch top 231 may be limited, which may further reduce the imaging or treatment efficiency of the medical system 200 and even affect the execution of the treatment.

Merely by way of example, when treating a patient with a breast tumor, a breast bracket may be used to lift the upper body of the patient to facilitate treatment. Before the treatment, the patient may be imaged by the imaging device 220 to determine the target region to be treated. Since the upper body of the patient is lifted, a position of the breast tumor may be higher than the isocenter plane of the imaging device 220. In the imaging procedure, the couch top 231 may be lowered to position the patient. For example, the couch top 231 may be moved to a relatively low position to position the breast tumor at the isocenter plane of the imaging device 220. The support portion 232-1 below the couch top 231 may limit the movement range of the couch top 231.

In some embodiments, a diameter of the bore and/or an outer diameter of the drum may be adjusted to increase the movement range of the at least a portion (e.g., the couch top 231, the support portion 232-1) of the couch 230. Taking the imaging device 220 as an example, a diameter of the bore 222 and an outer diameter of the drum 221 may be increased simultaneously. However, positions of other components (e.g., the ray tube 223, the detector 224, etc.) of the imaging device 220 may need to be adjusted accordingly. In addition, the increase of the outer diameter of the drum 221 may cause a size (e.g., a height) of the imaging device 220 to be increased, which may not only cause a simultaneous increase in a size of the housing 225, thereby resulting in an increase in the cost of manufacture, transportation, storage, installation, and/or maintenance, but also impose new demands on a size (e.g., a height) of the room for accommodating the imaging device 220. As another example, if the diameter of the bore 222 is increased and the outer diameter of the drum 221 is kept unchanged, a thickness of the drum 221 in a radial direction of the drum 221 may need to be reduced, which may cause insufficient mechanical strength and/or rigidity of the drum 221 and make it difficult for the drum 221 to carry or support various components (e.g., the ray tube 223, the detector 224, etc.) disposed therein, thereby reducing the safety, stability, and/or reliability of the drum 221 during the rotation of the drum 221.

According to some embodiments of the present disclosure, a cavity of a medical device is provided. The cavity may be configured such that the movement range of at least a portion of a couch in the cavity (e.g., a movement range in the vertical direction) may be increased, which may reduce the limitations on or difficulty of adjusting the position of the subject during the imaging and/or treatment procedure, thereby improving the treatment efficiency.

Figure 6A:
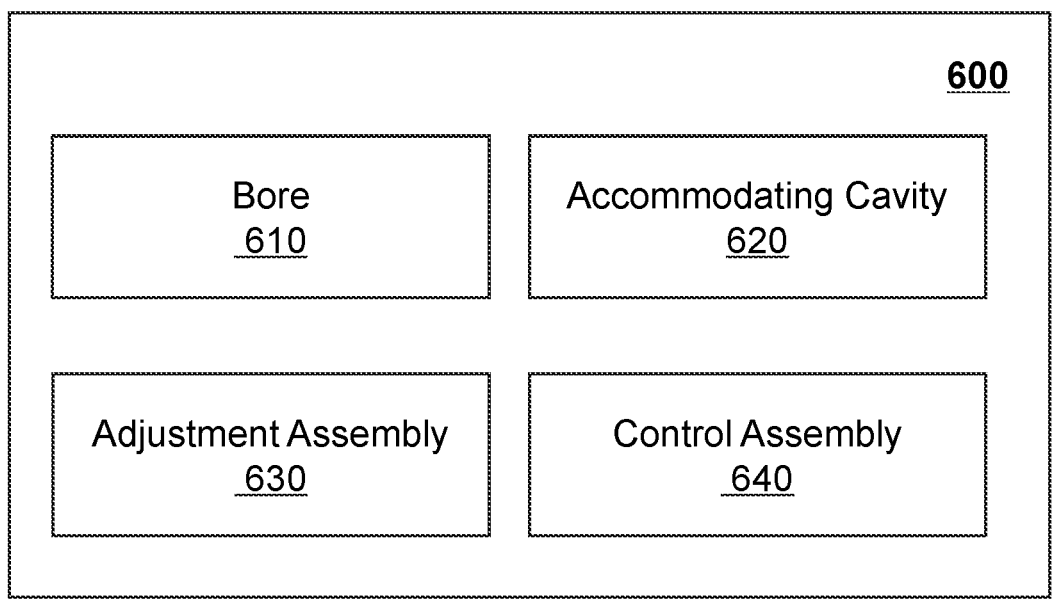
FIG. 6A is a schematic diagram illustrating exemplary components of an exemplary cavity according to some embodiments of the present disclosure.

FIG. 6A is a schematic diagram illustrating exemplary components of an exemplary cavity according to some embodiments of the present disclosure. In some embodiments, the cavity 600 may be a portion of a medical device. The medical device may include an imaging device, a radiation therapy device, or the like, or any combination thereof. As illustrated in FIG. 6A, the cavity 600 may include a bore 610, an accommodating cavity (also referred to as an "avoidance space") 620, an adjustment assembly 630, and a control assembly 640.

The bore 610 may be configured to accommodate a subject to be imaged and/or treated. For example, the bore 610 may be a space enclosed by a drum (e.g., the drum 720 illustrated in FIGS. 7-9, the drum 1020 illustrated in FIGS. 10-15, etc.). A shape of the bore 610 may be (substantially) a cylinder. As used herein, substantially, when used to qualify a feature (e.g., a shape, equivalent to), indicates that the deviation from the feature is below a threshold, e.g., 30%, 25%, 20%, 15%, 10%, 5%, etc. An axis direction of the cylinder may be parallel to the horizontal direction. At least one end of the drum may have an opening such that the bore 610 may have an entrance through which a couch carrying the subject moves into or out of the bore 610. The bore 610 may include a scanning region or a treatment region of the medical device. The subject or a portion thereof (e.g., an ROI, a target region, etc.) may be positioned at the scanning region or the treatment region for imaging or treatment.

The accommodating cavity 620 may be disposed on an inner wall of the bore 610. The inner wall of the bore 610 may also be referred to as an inner wall of the drum that defines the bore 610. The inner wall of the drum on which the accommodating cavity 620 is disposed refers to an inner wall of the drum that is close to or towards the subject. The accommodating cavity 620 may extend, from the entrance of the bore 610, along the axial direction of the bore 610. A length (also referred to as an "avoidance length") of the accommodating cavity 620 may be less than a length of the bore 610 in the axial direction.

Figure 6B:
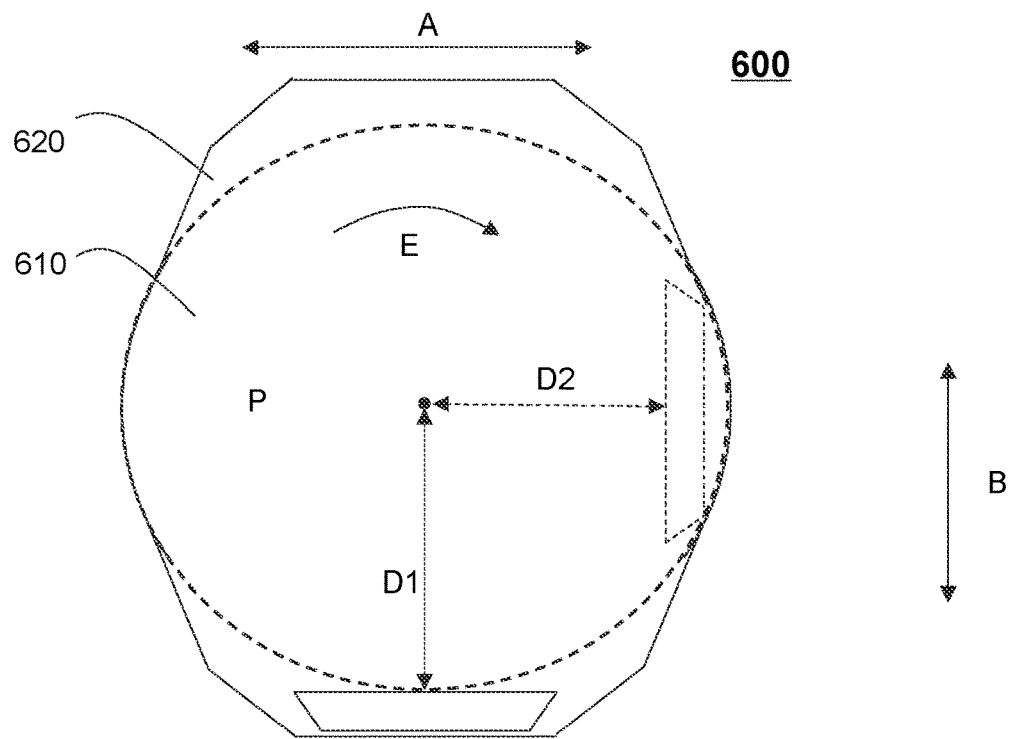
FIG. 6B illustrates an exemplary cross section of a cavity according to some embodiments of the present disclosure.

In some embodiments, the accommodating cavity 620 may be configured to form, with the bore 610, a connected space in which at least a portion of the couch is allowed to move along the axial direction of the bore 610. The connected space formed by the accommodating cavity 620 and the bore 610 may also be referred to as the cavity 600. An axial direction of the cavity 600 may be parallel to the axial direction of the bore 610. The at least a portion of the couch may move into or out of the cavity 600 along the axial direction of the bore 610 (or the cavity 600). In some embodiments, a cross section of the cavity 600 may be of a shape other than a circle. For example, the cross section of the cavity 600 may be polygonal. In some embodiments, a size of the cross section of the cavity 600 in a first direction may be different from a size of the cross section of the cavity 600 in a second direction. The first direction and the second direction may be radial directions of the bore 610 (or the cavity 600) and perpendicular to the axial direction of the bore 610. An included angle between the first direction and the second direction may be larger than 0. Accordingly, a movement range of the at least a portion of the couch in the first direction may be larger than a movement range of the at least a portion of the couch in the second direction. Merely by way of example, the first direction may be a vertical direction, and the second direction may be a horizontal direction. FIG. 6B illustrates an exemplary cross section of the cavity 600 according to some embodiments of the present disclosure. As illustrated in FIG. 6B, the movement range D1 of the at least a portion of the couch in the vertical direction B may be larger than the movement range D2 of the at least a portion of the couch in the horizontal direction A. In some embodiments, the at least a portion of the couch may be raised or lowered in the bore 610 along the vertical direction B, and accordingly the movement range D2 refers to a movement range of the at least a portion of the couch along the vertical direction B when the cavity 600 has rotated 90 degrees along the clockwise direction E compared to the configuration illustrated in FIG. 6B.

In some embodiments, the accommodating cavity 620 may be configured to provide an accommodating space for at least a portion of the couch in a radial direction of the bore. That is, the accommodating cavity 620 may be used as an extra space for expanding the bore 610. In such cases, compared with a bore without the accommodating cavity 620, a movement range of the at least a portion of the couch in the bore 610 (or the cavity 600) in the radial direction may be increased. In some embodiments, the at least a portion of the couch may move along the vertical direction B. Correspondingly, the accommodating cavity 620 may be used to increase the movement range of the at least a portion of the couch in the vertical direction. Merely by way of example, the at least a portion of the couch may be raised or lowered along the vertical direction to adjust the position of the subject, or a portion thereof (e.g., an ROI of the subject). The accommodating cavity 620 may be configured to accommodate the at least a portion of the couch in the vertical direction such that the movement range may be increased. For example, the accommodating cavity 620 may be configured to accommodate a couch top of the couch. A width of the accommodating cavity 620 may be larger than a width of the couch top. As another example, the couch may include a support portion (e.g., the support portion 232-1 illustrated in FIG. 2). The support portion may be configured to support the couch top. The accommodating cavity 620 may be configured to accommodate the support portion. A width of the accommodating cavity may be larger than a width of the support portion.

Figure 6C:
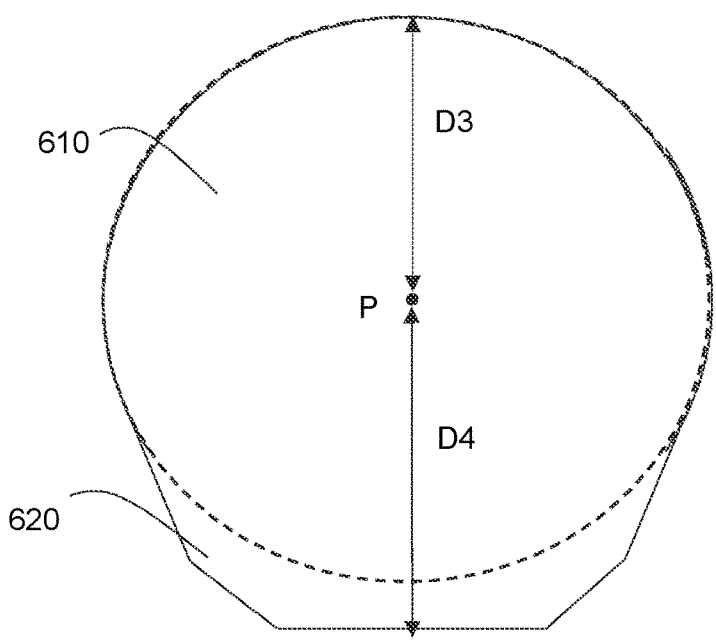
FIG. 6C illustrates another exemplary cross section of a cavity according to some embodiments of the present disclosure.

In some embodiments, a shape of a cross section of the bore 610 may be axisymmetric about a vertical axis. A center line (e.g., the center line L illustrated in FIG. 7) of the bore 610 in the axial direction may pass through a center (e.g., the center P illustrated in FIG. 6B, FIG. 6C and FIG. 8) of the cross section. FIG. 6C illustrates another exemplary cross section of the cavity 600 according to some embodiments of the present disclosure. In some embodiments, as illustrated in FIG. 6C, the accommodating cavity 620 may be disposed at a lower inner wall of the bore 610 below a center line (e.g., the center line L illustrated in FIG. 7) of the bore 610 along the vertical direction B of the bore 610. In such cases, a distance (e.g., the distance D3 illustrated in FIG. 6C) between the center line of the bore 610 in the axial direction and an upper inner wall of the cavity 600 (i.e., the upper inner wall of the bore 610 above the center line of the bore 610 along the vertical direction B of the bore 610) may be less than a distance (e.g., the distance D4 illustrated in FIG. 6C) between the center line and a lower inner wall of the cavity 600 (also referred to as "a lower inner wall of the bore 610").

In some embodiments, the cavity 600 may further include a second accommodating cavity. The second accommodating cavity may be configured to form, in combination with the bore 610 and the accommodating cavity 620, the connected space. In some embodiments, the second accommodating cavity may be disposed on an inner wall of the bore 610 and opposite to the accommodating cavity 620. For example, the accommodating cavity 620 may be disposed on the lower inner wall of the bore 610 below the center line of the bore 610 along the vertical direction B of the bore 610, and the second accommodating cavity may be disposed on the upper inner wall of the bore 610 above the center line of the bore 610 along the vertical direction of the bore 610. In such cases, the accommodating cavity 620 and the second accommodating cavity may be symmetrical with respect to the center line of the bore 610 along the vertical direction B of the bore 610, which may increase the balance and safety of the medical device during a rotation of the drum. It should be noted that, a count and positions of the accommodating cavities may be adjusted according to actual needs, which are not limited in the present disclosure. More descriptions regarding the accommodating cavity 620 may be found elsewhere in the present disclosure (e.g., FIGS. 7-16 and the description thereof).

The adjustment assembly 630 may be configured to adjust an opening and a closing of the accommodating cavity 620. For example, the adjustment assembly 630 may be or include a cover configured to cover the opening of the accommodating cavity 620 (e.g., the opening 1012-3 illustrated in FIG. 13). The adjustment assembly 630 may be disposed in the accommodating cavity 620. In some embodiments, the adjustment assembly 630 may be configured to move in the vertical direction B to reach a raised configuration that corresponds to a closed state of the accommodating cavity 620 or a retracted configuration that corresponds to an open state of the accommodating cavity 620. When the adjustment assembly 630 is at the raised configuration, the adjustment assembly 630 (or the cover) may be raised to cover the opening of the accommodating cavity 620. When the adjustment assembly 630 is at the retracted configuration, the adjustment assembly 630 (or the cover) may retract into the accommodating cavity 620. In some embodiments, the adjustment assembly 630 may be configured to move in the axial direction to reach an extended configuration that corresponds to a closed state of the accommodating cavity 620 or a retracted configuration that corresponds to an open state of the accommodating cavity 620. When the adjustment assembly 630 is at the extended configuration, the cover may extend to cover the opening of the accommodating cavity 620. When the adjustment assembly 630 is at the retracted configuration, the adjustment assembly 630 (or the cover) may retract into the accommodating cavity 620. In the closed state, the accommodating cavity 620 may be inaccessible to the at least a portion of the couch. In the open state, the accommodating cavity 620 may be accessible to the at least a portion of the couch. A distance (e.g., the distance D5 illustrated in FIG. 13) between the adjustment assembly 630 and an opening of the accommodating cavity 620 along the vertical direction may be larger than 0. The at least a portion of the couch may be accommodated by the accommodating cavity 620.

The control assembly 640 may be configured to control the adjustment assembly 630. For example, the control assembly 640 may control the adjustment assembly 630 to switch between the raised configuration (or the closed state) and the retracted configuration (or the open state). Merely by way of example, the control assembly 640 may be an individual assembly in communication with a processing device (e.g., the processing device 140) of the medical device. In response to an instruction received from the processing device, the control assembly 640 may control the adjustment assembly 630. As another example, the control assembly 640 may be integrated into the processing device of the medical device. More descriptions regarding the control assembly 640 and the adjustment assembly 630 may be found elsewhere in the present disclosure (e.g., FIGS. 10-15 and the description thereof).

It should be noted that the above description of the cavity 600 is merely provided for the purposes of illustration and not intended to limit the scope of the present disclosure. For persons having ordinary skill in the art, multiple variations and modifications may be made under the teachings of the present disclosure. However, those variations and modifications do not depart from the scope of the present disclosure. In some embodiments, one or more other components may be included in the cavity 600 or one or more components included in the cavity 600 may be omitted. For example, the control assembly 640 may be omitted. The adjustment assembly 630 may be controlled by an operator to switch between the closed state and the open state. As another example, the adjustment assembly 630 may be omitted. The accommodating cavity 620 may always remain open to simplify operation.

In addition, the term "direction" (e.g., the horizontal direction, the vertical direction, the clockwise direction, etc.) described in the present disclosure may be a relative concept and not intended to limit the scope of the present disclosure.

Figure 7:
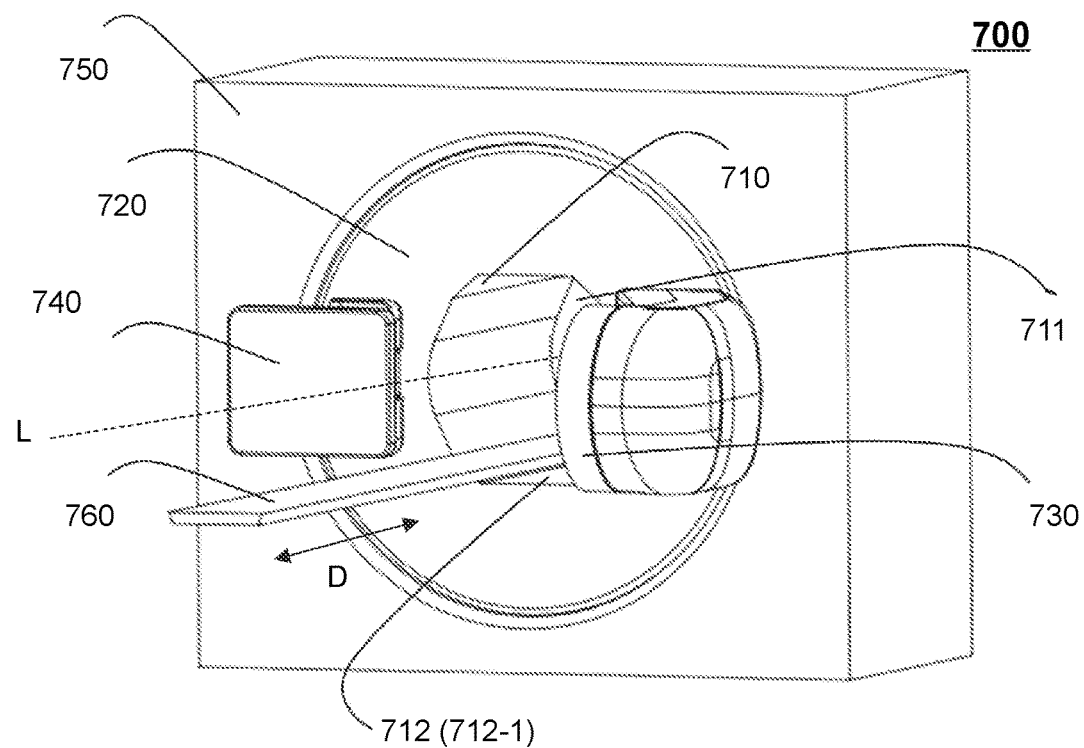
FIG. 7 is a schematic diagram illustrating an exemplary medical device with a cavity according to some embodiments of the present disclosure.
Figure 8:
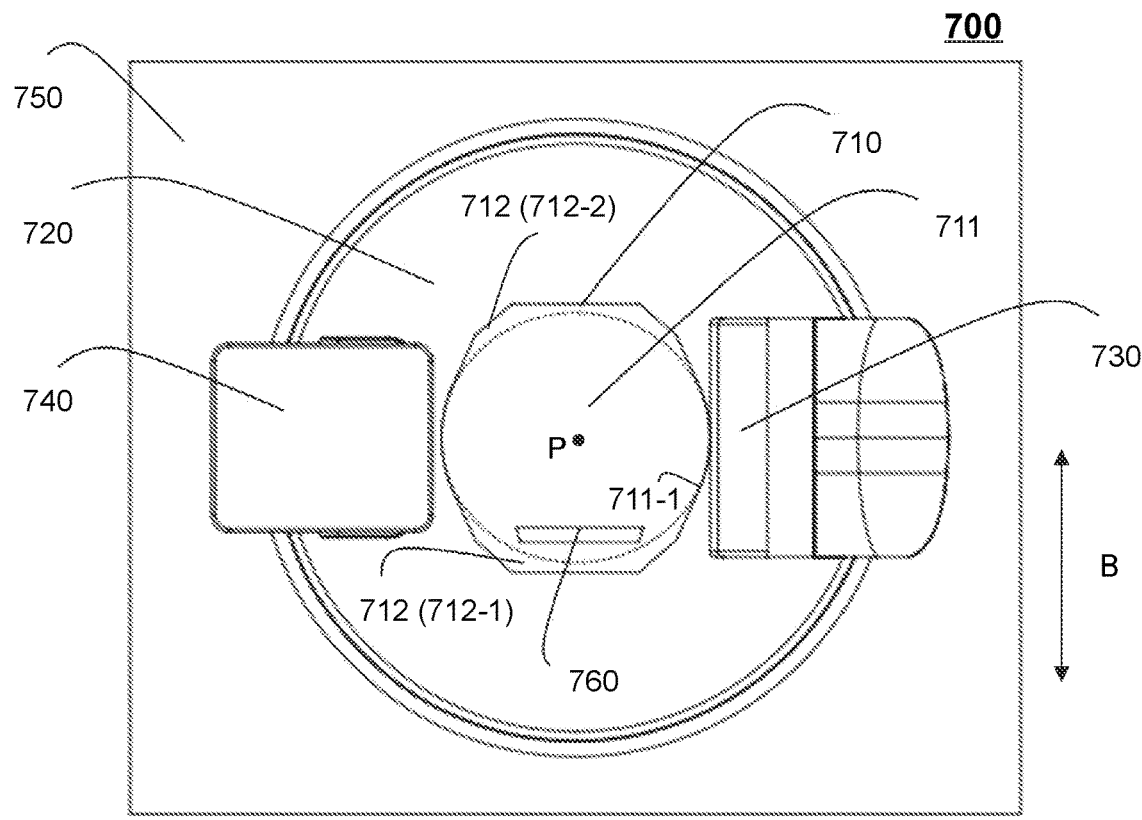
FIG. 8 is a schematic diagram illustrating a front view of the medical device illustrated in FIG. 7.

FIG. 7 is a schematic diagram illustrating an exemplary medical device with a cavity according to some embodiments of the present disclosure. FIG. 8 is a schematic diagram illustrating a front view of the medical device illustrated in FIG. 7. The medical device 700 may be an exemplary embodiment of the medical device 110 as described in connection with FIG. 1 or the medical device including the cavity 600 as described in connection with FIG. 6A. For illustration purposes only, the medical device 700 shown in FIG. 7 and FIG. 8 may be a radiation therapy device. As illustrated in FIG. 7 and FIG. 8, the medical device 700 may include a cavity 710, a drum 720, a treatment head 730, an electronic portal imaging device 740, and a housing 750. In some embodiments, the drum 720, the treatment head 730, the electronic portal imaging device 740, and the housing 750 may be the same as or similar to the drum 211, the treatment head 214, the electronic portal imaging device 216, and the housing 215 illustrated in FIG. 2, respectively, which are not repeated herein.

The cavity 710 may include a bore 711 and an accommodating cavity 712. As illustrated in FIG. 7 and FIG. 8, a cross section of the bore 711 may be circular. A couch top 760 of a couch may move into the bore 711 through an entrance of the bore 711. The accommodating cavity 712 may be disposed on an inner wall 711-1 of the bore 711. For example, the accommodating cavity 712 may extend, from the entrance of the bore 711, along an axial direction D of the bore 711. A length of the accommodating cavity 712 may be less than or equal to a length of the bore 711 in the axial direction D. In some embodiments, the accommodating cavity 712 may include a first accommodating cavity 712-1 and a second accommodating cavity 712-2. The first accommodating cavity 712-1 and the second accommodating cavity 712-2 may be disposed opposite each other. In some embodiments, the first accommodating cavity 712-1 and the second accommodating cavity 712-2 may be symmetrical with respect to a center line of bore 711, which may be convenient for machining and may increase the balance and safety of the medical device 700 during a rotation of the drum 720.

In some embodiments, the accommodating cavity 712 may be used as an extra space for expanding the bore 711, which may increase the movement range of the couch top 760. For example, as illustrated in FIG. 7 and FIG. 8, the bore 711 and the accommodating cavity 712 may form a connected space (i.e., the cavity 710). The couch top 760 may move into or out of the connected space along the axial direction D. An area of a cross section of the cavity 710 may be larger than that of the bore 711. For instance, as illustrated in FIG. 8, the cross section of the cavity 710 may be polygonal. The area of the cross section of the cavity 710 may be larger than that of the bore 711. In such cases, compared with a bore 711 without the accommodating cavity 712, a movement range of the couch top 760 in the bore 711 (or the cavity 710) may be increased.

Figure 9:
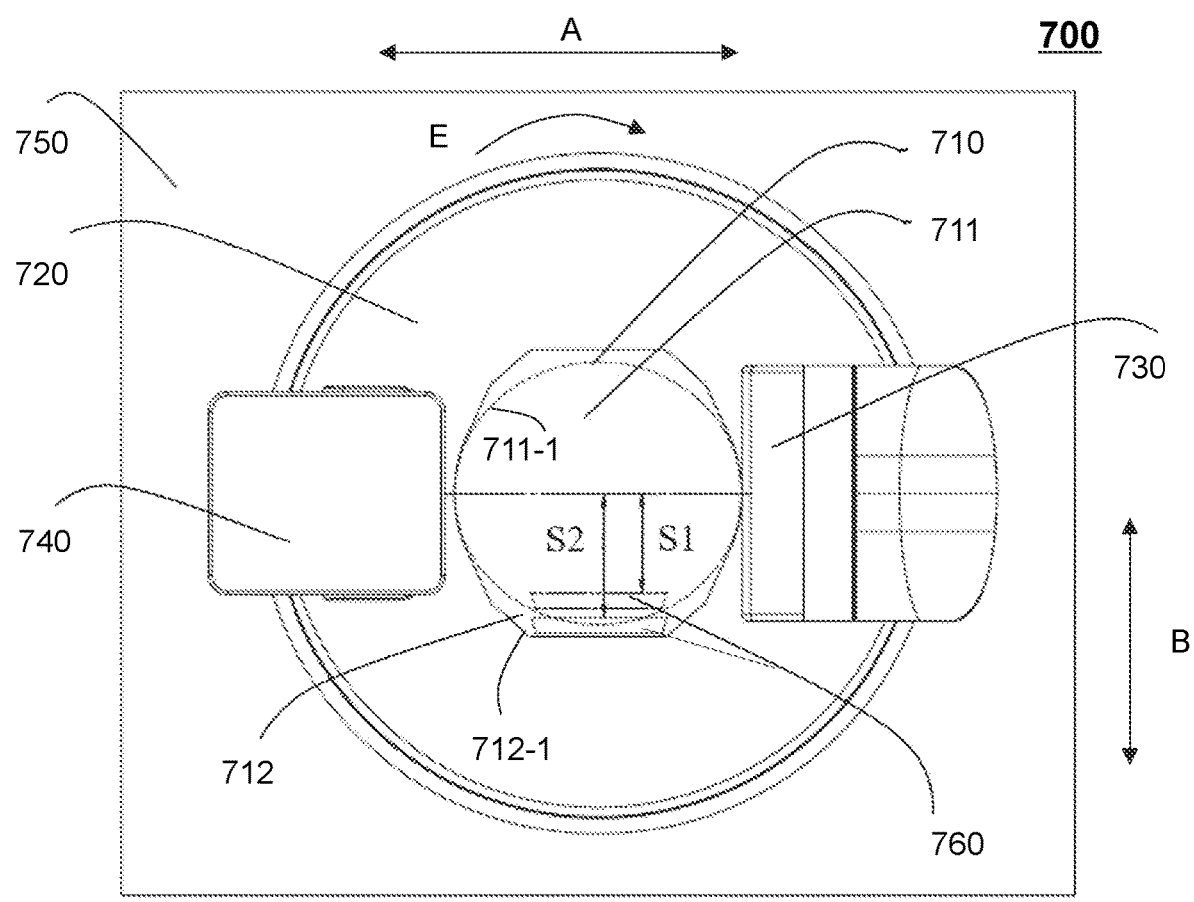
FIG. 9 is a schematic diagram illustrating a front view of the medical device illustrated in FIG. 7.

Merely by way of example, FIG. 9 is a schematic diagram illustrating a front view of the medical device illustrated in FIG. 7. As illustrated in FIG. 9, the couch top 760 may be raised or lowered along the vertical direction B to adjust the position of the subject or a portion thereof. The accommodating cavity 712 may be configured to accommodate the couch top 760 in the vertical direction B such that the movement range may be increased. In some embodiments, to accommodate the couch top 760, the accommodating cavity 712 may be positioned at a bottom portion of the cavity 710. As used herein, the accommodating cavity 712 being positioned at the bottom portion of the cavity 710 refers to that the accommodating cavity 712 (e.g., the first accommodating cavity 712-1 or the second accommodating cavity 712-2) is positioned at the lowest position in the cavity 710 in the vertical direction B. For example, in an initial state (e.g., a state illustrated in FIG. 5) of the medical device 700, the treatment head 730 may be located at the highest position, the accommodating cavity 712 may be disposed on a radial direction of the bore 711, and a connection line between the treatment head 730 and the electronic portal imaging device 740 may be perpendicular to the radial direction. The medical device 700 illustrated in FIG. 9 may be in a state in which the drum 720 has rotated 90 degrees along the clockwise direction E compared to the configuration illustrated in FIG. 4 and FIG. 5. In such cases, the accommodating cavity 712 may be positioned at the bottom portion of the cavity 710 so as to accommodate the couch top 760. As illustrated in FIG. 9, a shape of the bore 711 without the accommodating cavity 712 may be a circle shown by the dotted line. In the bore 711 without the accommodating cavity 712, the couch top 760 may descend along the vertical direction B until the couch top 760 gets in contact with the inner wall 711-1 of the bore 711. In the vertical direction B. S1 may be the maximum movement range of the couch top 760 in the bore 711 from a center of the cross section of the bore 711. In the bore 711 with the accommodating cavity 712 (i.e., the cavity 710), the accommodating cavity 712 may accommodate the couch top 760 in the vertical direction B. The couch top 760 may descend along the vertical direction B until the couch top 760 gets in contact with the inner wall 712-1 of the accommodating cavity 712. In the vertical direction B. S2 may be the maximum movement range of the couch top 760 in the cavity 710 from the center of the cross section of the bore 711. S2 is larger than S1. Accordingly, the accommodating cavity 712 may accommodate the couch top 760 in the vertical direction B, thereby increasing the movement range of the couch top 760. In some embodiments, the accommodating cavity 712 may have a depth (also referred to as an "avoidance depth") in the radial direction of the bore 711. A width of the accommodating cavity 712 may be larger than a width of the couch top 760. Alternatively or additionally, the couch may also include a support portion (e.g., the support portion 232-1 illustrated in FIG. 2). The accommodating cavity 712 may be configured to accommodate the support portion. A width of the accommodating cavity 712 may be larger than a width of the support portion.

In some embodiments, a position of the accommodating cavity 712 may be configured such that other components of the medical device 700 are not interfered. For example, the position of the accommodating cavity 712 may be far away from the treatment head 730 and/or the electronic portal imaging device 740. For instance, as illustrated in FIG. 8, the accommodating cavity 712 may be disposed on a radial direction of the bore 711, and the radial direction may be perpendicular to a connection line between the treatment head 730 and the electronic portal imaging device 740. In such cases, the couch top 760 may not interfere with the treatment head 730 or the electronic portal imaging device 740 during a movement of the couch top 760. Furthermore, since the position of the accommodating cavity 712 does not interfere with other components of the medical device 700, the medical device of the present disclosure may be obtained without any changes to other components (e.g., the treatment head 730, the electronic portal imaging device 740, etc.) of a traditional medical device, which may simplify the manufacturing process of the medical device of the present disclosure. Moreover, compared to the traditional medical device, a size (e.g., a volume) of the medical device of the present disclosure does not need to be increased, and accordingly the space occupied by the medical device does not increase. In some embodiments, since the configuration of the cavity does not change the position of other components of the medical device 700, a movement range of the couch top 760 in a first direction in the cavity 710 may be larger than a movement range of the couch top 760 in a second direction. The first direction and the second direction may be radial directions of the bore 711 (or the cavity 710) and perpendicular to the axial direction D of the bore 711. An included angle between the first direction and the second direction may be larger than 0. The first direction may be the vertical direction B. Merely by way of example, the second direction is the horizontal direction A as illustrated in FIGS. 7-9, a radial length of the cross section of the cavity 710 in the vertical direction B may be larger than a radial length of the cross section of the cavity 710 in the horizontal direction A. In such cases, a movement range of the couch top 760 in the first direction may be larger than a movement range of the couch top 760 in the second direction.

It should be noted that the example illustrated in FIG. 7 and FIG. 8 and the above description thereof are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the medical device 700 may include one or more additional components and/or one or more components of the medical device 700 described above may be omitted. For example, the medical device 700 (or the cavity 710) may include an adjustment assembly configured to adjust an opening and a closing of the accommodating cavity 712. As another example, the medical device 700 (or the cavity 710) may include a control assembly configured to control the adjustment assembly.

In addition, the count, the position, the shape, and/or the size (e.g., a length, a depth, a width, etc.) of the accommodating cavity 712 as shown in FIG. 7 and FIG. 8 are illustrative, the cavity 710 may include any count of accommodating cavities, and the accommodating cavity 712 may be disposed at any position and have any size and/or shape. For example, one of the first accommodating cavity 712-1 and the second accommodating cavity 712-2 may be omitted. The cavity 710 may include only one accommodating cavity. As another example, the cross section of the accommodating cavity 712 (e.g., the first accommodating cavity 712-1 or the second accommodating cavity 712-2) may be rectangular. As a further example, the accommodating cavity 712 may be configured such that the cross section of the cavity 710 has a shape of a regular polygon.

Figure 10:
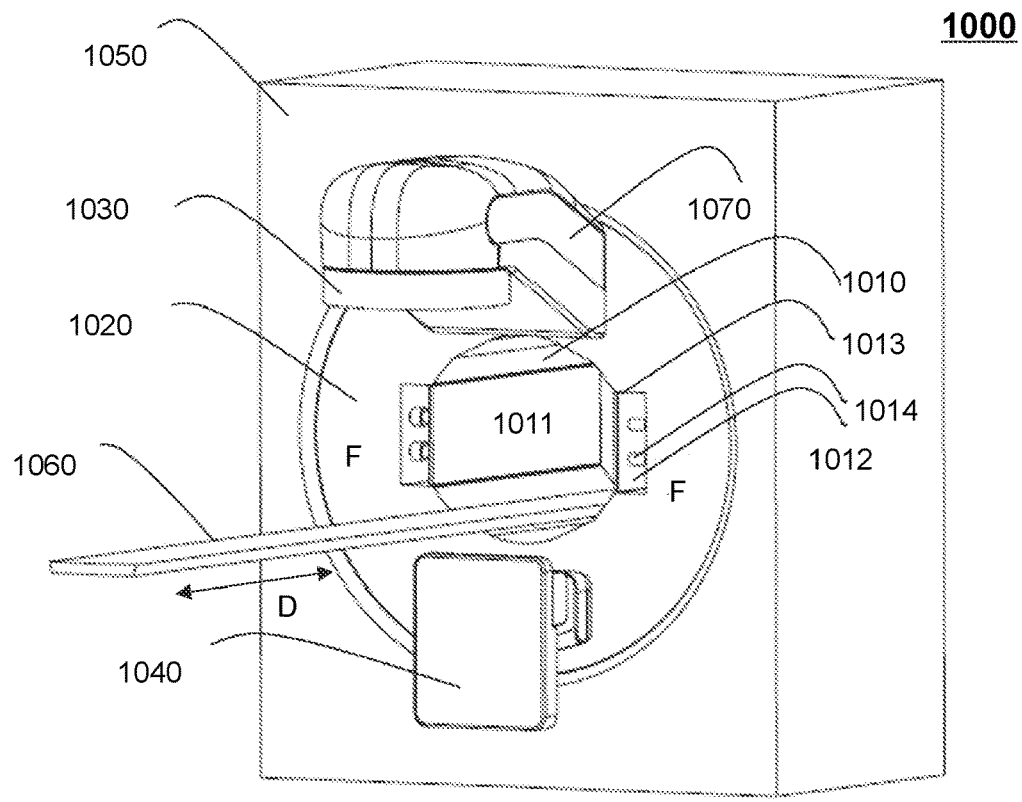
FIG. 10 is a schematic diagram illustrating another exemplary medical device with a cavity according to some embodiments of the present disclosure.
Figure 11:
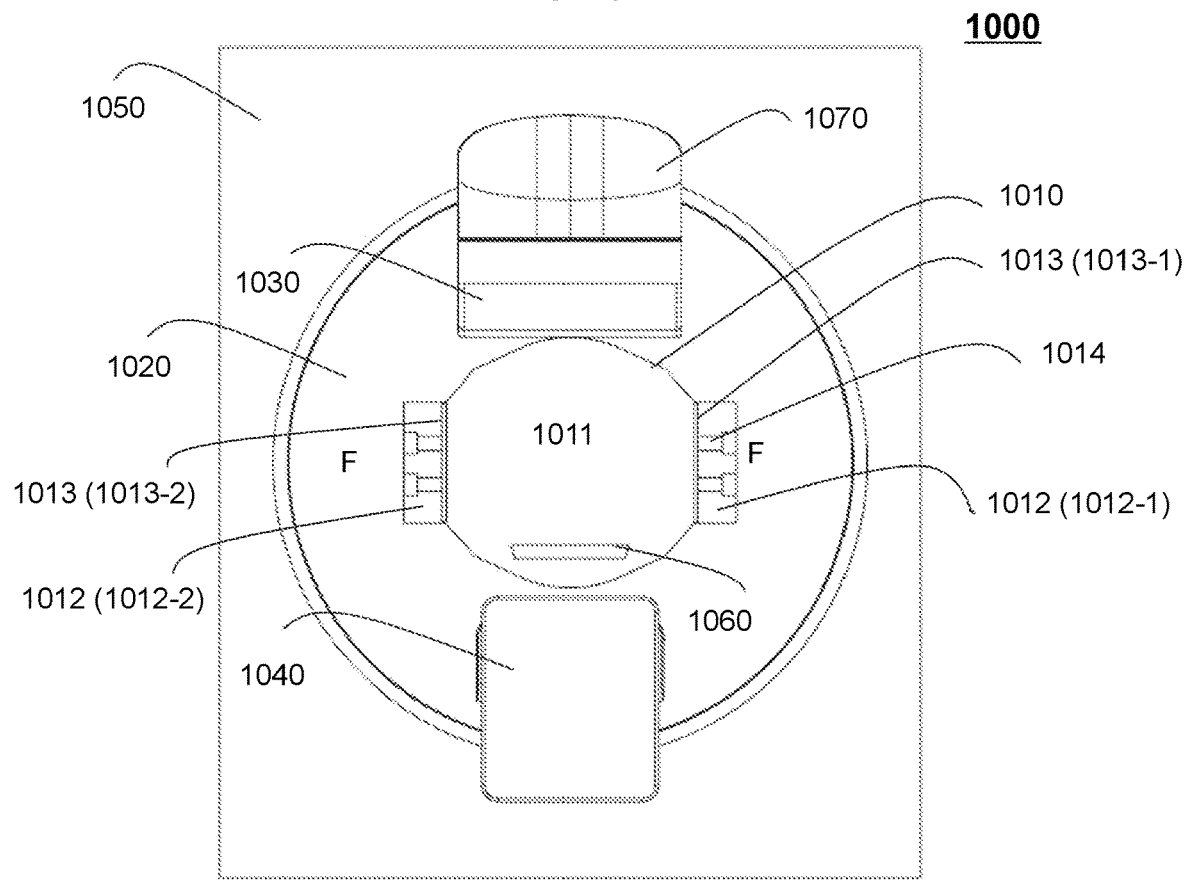
FIG. 11 is a schematic diagram illustrating a front view of the medical device illustrated in FIG. 10.

FIG. 10 is a schematic diagram illustrating another exemplary medical device with a cavity according to some embodiments of the present disclosure. FIG. 11 is a schematic diagram illustrating a front view of the medical device illustrated in FIG. 10. The medical device 1000 may be an exemplary embodiment of the medical device 110 as described in connection with FIG. 1 or the medical device including the cavity 600 as described in connection with FIG. 6A. For illustration purposes only, the medical device 1000 shown in FIG. 10 and FIG. 11 may be a radiation therapy device. As illustrated in FIG. 10 or FIG. 11, the medical device 1000 may include a cavity 1010, a drum 1020, a treatment arm 1070, a treatment head 1030, an electronic portal imaging device 1040, and a housing 1050. In some embodiments, the drum 1020, the treatment arm 1070, the treatment head 1030, the electronic portal imaging device 1040, and the housing 1050 may be the same as or similar to the drum 211, the treatment arm 213, the treatment head 214, the electronic portal imaging device 216, and the housing 215 illustrated in FIG. 2, respectively, which are not repeated herein. In some embodiments, the medical device 1000 illustrated in FIG. 10 and FIG. 11 may be in an initial state in which the drum 1020 does not rotate (or rotates 0 degrees).

The cavity 1010 may include a bore 1011 and an accommodating cavity 1012. As illustrated in FIG. 10 and FIG. 11, the bore 1011 and the accommodating cavity 1012 may form a connected space (i.e., the cavity 1010). The couch top 1060 may move into or out of the connected space along the axial direction D through an entrance of the bore 1011. A shape of the cross section of the bore 1011 may be (substantially) a polygon. The accommodating cavity 1012 may be disposed on an inner wall of the bore 1011. For example, the accommodating cavity 1012 may extend, from the entrance of the bore 1011, along the axial direction D of the bore 1011. A length of the accommodating cavity 1012 may be less than or equal to a length of the bore 1011 in the axial direction D. In some embodiments, as illustrated in FIG. 11, the accommodating cavity 1012 may be disposed on a radial direction of the bore 1011, and the radial direction may be perpendicular to a connection line between the treatment head 1030 and the electronic portal imaging device 1040. In such cases, the couch top 1060 may not interfere with the treatment head 1030 or the electronic portal imaging device 1040 during a movement of the couch top 1060. In some embodiments, the accommodating cavity 1012 may include a first accommodating cavity 1012-1 and a second accommodating cavity 1012-2. The first accommodating cavity 1012-1 and the second accommodating cavity 1012-2 may be disposed opposite each other. As illustrated in FIG. 10 and FIG. 11, the accommodating cavity 1012 may form a groove(s) on an inner wall of the drum 1020. A cross section of the accommodating cavity 1012 may have a shape(s) of a rectangle(s) that protrudes outward relative to the cross section of the bore 1011.

Figure 12:
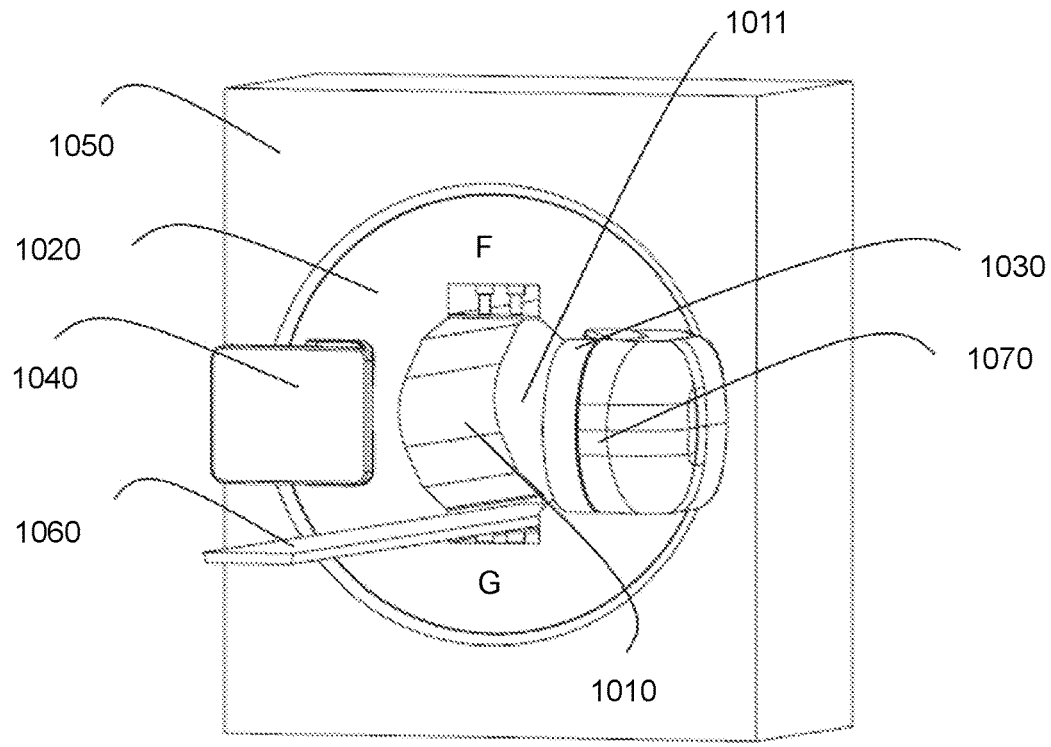
FIG. 12 is a schematic diagram illustrating another exemplary state of the medical device illustrated in FIG. 10.
Figure 13:
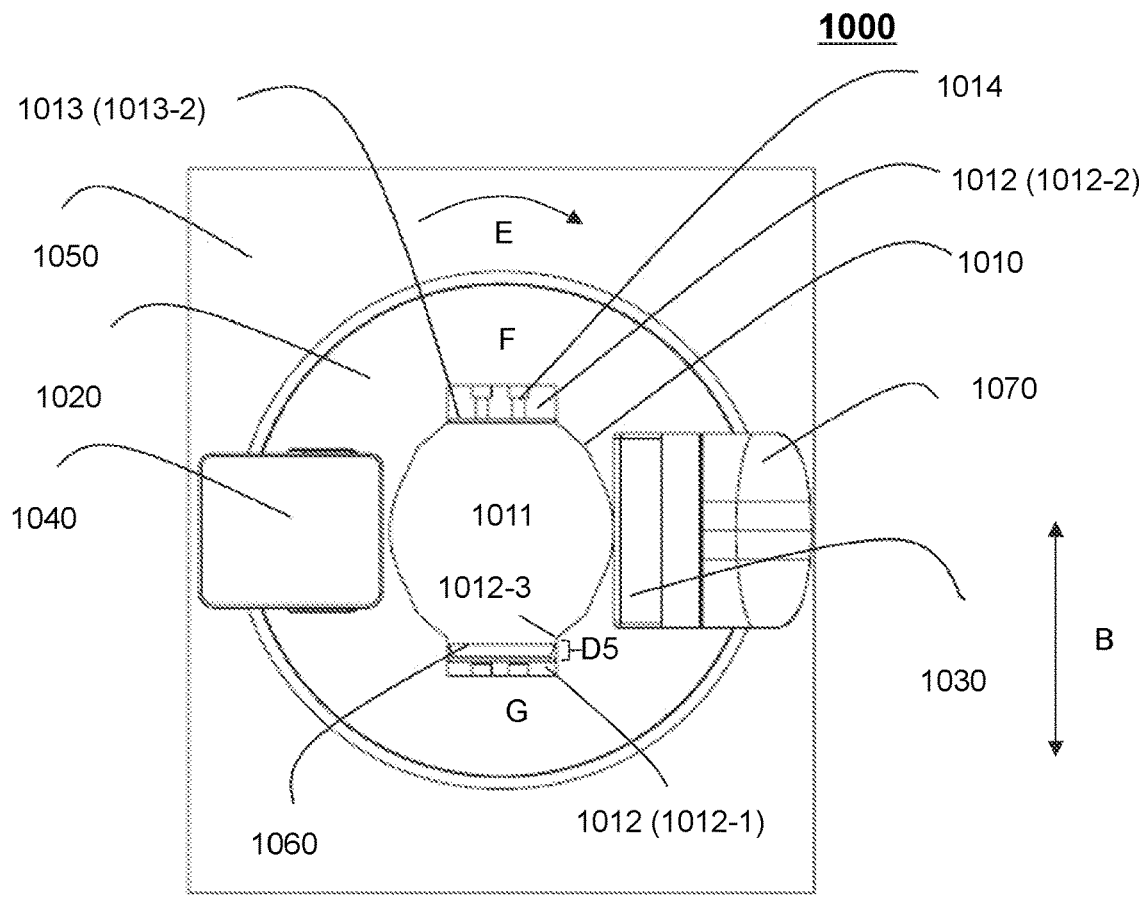
FIG. 13 is a schematic diagram illustrating a front view of the medical device illustrated in FIG. 12.

In some embodiments, as illustrated in FIG. 10 and FIG. 11, the cavity 1010 may include an adjustment assembly 1013. The adjustment assembly 1013 may be configured to adjust an opening and a closing of the accommodating cavity 1012. Merely by way of example, FIG. 12 is a schematic diagram illustrating another exemplary state of the medical device illustrated in FIG. 10. FIG. 13 is a schematic diagram illustrating a front view of the medical device illustrated in FIG. 12. As illustrated in FIG. 12 and FIG. 13, the medical device 1000 may be in a state in which the drum 1020 has rotated 90 degrees along the clockwise direction E such that the accommodating cavity 1012 (e.g., the first accommodating cavity 1012-1) may be positioned at the bottom portion of the cavity 1010. The adjustment assembly 1013 may be or include a cover configured to cover the opening 1012-3 of the accommodating cavity 1012. For example, the cover may be disposed in the accommodating cavity 1012 and may be configured to move in the vertical direction B to reach a raised configuration F or a retracted configuration G. At the raised configuration F, the cover may be raised to cover the opening 1012-3 of the accommodating cavity 1012 such that the accommodating cavity 1012 may be in a closed state. At the retracted configuration G, the cover may retract into the accommodating cavity 1012 such that the accommodating cavity 1012 may be in an open state. In such cases, a distance D5 between the adjustment assembly 1013 and the opening 1012-3 of the accommodating cavity 1012 may be larger than 0. When the couch top 1060 is lowered along the vertical direction B, at least a portion of the couch top 1060 may be accommodated by the accommodating cavity 1012, which may increase the movement range (e.g., a descending height) of the couch top 1060 in the vertical direction B.

Figure 14:
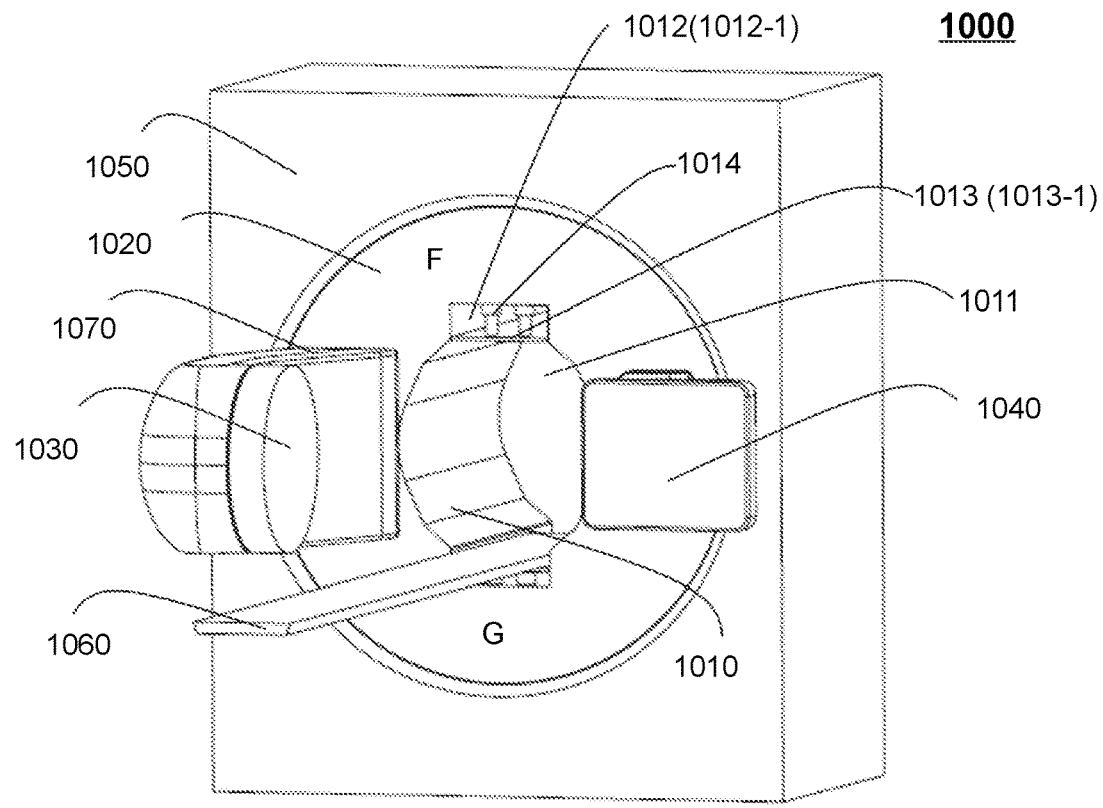
FIG. 14 is a schematic diagram illustrating another exemplary state of the medical device illustrated in FIG. 10.
Figure 15:
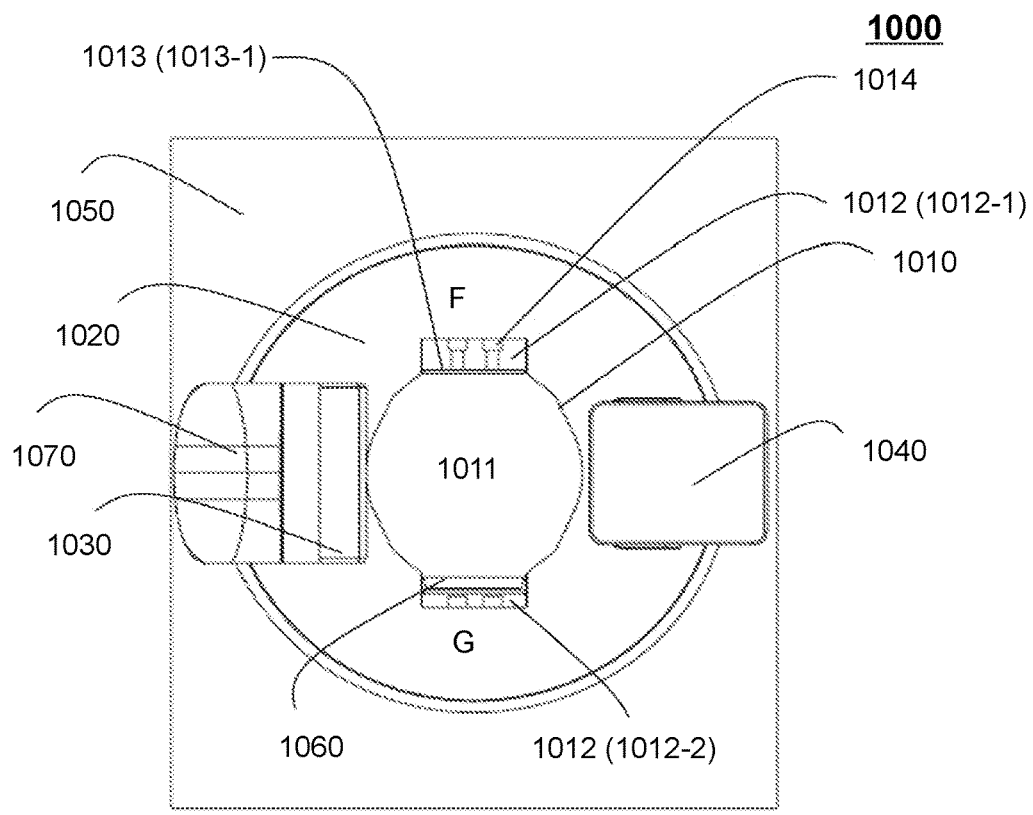
FIG. 15 is a schematic diagram illustrating a front view of the medical device illustrated in FIG. 14.

In some embodiments, a count of the adjustment assembly 1013 may correspond to a count of the accommodating cavity 1012. For example, the adjustment assembly 1013 may include a first adjustment assembly 1013-1 (e.g., a first cover) corresponding to the first accommodating cavity 1012-1 and a second adjustment assembly 1013-2 (e.g., a second cover) corresponding to the second accommodating cavity 1012-2. In some embodiments, the adjustment assembly 1013 may be at the same configuration or different configurations. For example, both the first adjustment assembly 1013-1 and the second adjustment assembly 1013-2 may be at the retracted configuration G. As another example, as illustrated in FIG. 12 or FIG. 13, the second adjustment assembly 1013-2 may be at the raised configuration F, and the first adjustment assembly 1013-1 may be at the retracted configuration G such that the couch top 1060 may be accommodated by the first accommodating cavity 1012-1. As a further example, FIG. 14 is a schematic diagram illustrating another exemplary state of the medical device illustrated in FIG. 10. FIG. 15 is a schematic diagram illustrating a front view of the medical device illustrated in FIG. 14. As illustrated in FIG. 14 and FIG. 15, the medical device 1000 may be in a state in which the drum 1020 has rotated 270 degrees along the clockwise direction E such that the accommodating cavity 1012 (e.g., the second accommodating cavity 1012-2) may be positioned at the bottom portion of the cavity 1010. To increase the movement range of the couch top 1060 in the vertical direction, the first adjustment assembly 1013-1 may be at the raised configuration F, and the second adjustment assembly 1013-2 may be at the retracted configuration G such that the couch top 1060 may be accommodated by the second accommodating cavity 1012-2.

In some embodiments, a shape and/or material of the adjustment assembly 1013 may be configured to fit with the bore 1011 and/or the accommodating cavity 1012. For example, the cross section of the bore 1011 may be a circle with one or more notches at the accommodating cavity 1012. Correspondingly, the cover may have an arc surface. When the cover is at the raised configuration F, the surface of the cover may compensate for the notches such that the cross section of the bore 1011 may be a complete circle. As another example, the cover may be made of elastic materials such that the cover may be deformed (e.g., stretched, compressed, etc.) under an action of force to achieve the raised configuration F or the retracted configuration G. As a further example, the cover may be made of inelastic materials and may change its position under an action of force to achieve the raised configuration F or the retracted configuration G. If the cross section of the accommodating cavity 1012 is rectangular, a width of the cover in the radial direction of the bore 1011 may be less than a width of the accommodating cavity 1012, and a length of the cover in the axial direction D of the bore 1011 may be less than a length of the accommodating cavity 1012. In some embodiments, the cover may have a simple structure, which may simplify the manufacturing process of the medical device of the present disclosure.

In some embodiments, the cavity 1010 may include a connection assembly 1014. The connection assembly 1014 may be configured to connect the adjustment assembly 1013 to an inner wall of the accommodating cavity 1012. For example, as illustrated in FIGS. 10-13, the connection assembly 1014 may connect the cover to a bottom wall of the accommodating cavity 1012. In such cases, unexpected movement or falling of the cover caused by a rotation of the drum 1020 may be avoided or reduced, thereby preventing the subject from being injured and improving the safety of the medical device 1000. In some embodiments, the connection assembly 1014 may be operable to accomplish a switch between the raised configuration F and the retracted configuration G of the adjustment assembly 1013. For example, the connection assembly 1014 may include one or more telescopic rods. The one or more telescopic rods may extend to raise the cover such that the cover may be at the raised configuration F. And the one or more telescopic rods may compress to retract the cover such that the cover may be at the retracted configuration G. As another example, the connection assembly 1014 may include a collapsible component (e.g., a component including scissor mechanisms or pantograph mechanisms). The collapsible component may extend to raise the cover such that the cover may be at the raised configuration F. And the collapsible component may compress to retract the cover such that the cover may be at the retracted configuration G.

In some embodiments, the cavity 1010 may include a control assembly (not shown). The control assembly may be configured to control the adjustment assembly 1013 to switch between the raised configuration F and the retracted configuration G. For example, the control assembly may control the adjustment assembly 1013 based on instructions. Merely by way of example, when the movement range (e.g., the descending height) of the couch top 1060 needs to be increased, the control assembly may control the adjustment assembly 1013 to switch to retracted configuration G. And when the movement range of the couch top 1060 does not need to be increased, the control assembly may control the adjustment assembly 1013 to switch to the raised configuration F. In some embodiments, the control assembly may be an individual assembly in communication with a processing device (e.g., the processing device 140) of the medical device 1000 via a wired connection or a wireless connection. In response to an instruction received from the processing device, the control assembly may control the adjustment assembly 1013 to switch to a corresponding configuration. In some embodiments, the control assembly may be integrated into the processing device of the medical device 1000.

It should be noted that the example illustrated in FIGS. 10-15 and the above description thereof are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the medical device 1000 may include one or more additional components and/or one or more components of the medical device 1000 described above may be omitted. For example, the cover and the connection assembly 1014 illustrated in FIGS. 10-15 may be omitted. The adjustment assembly 1013 may include an airbag with a certain rigidity. Correspondingly, the control assembly may include an inflation/suction apparatus (e.g., an inflation/suction pump) in connection and/or controlled by the processing device of the medical device 1000. When the movement range of the couch top 1060 does not need to be increased, the inflation/suction apparatus may inflate the airbag such that the accommodating cavity 1012 may be filled by the airbag. Alternatively or additionally, when the airbag is filled with gas, a surface of the airbag facing the bore 1011 may be adapted to the opening 1012-3 of the accommodating cavity 1012. And when the movement range of the couch top 1060 needs to be increased, the inflation/suction apparatus may suction gas from the inflated airbag such that the airbag may fit on the inner wall of the accommodating cavity 1012. Then the couch top 1060 may be accommodated by the accommodating cavity 1012.

In addition, the count, the position, the shape, and/or the size (e.g., a length, a depth, a width, etc.) of a component of the cavity 1010 as shown in FIGS. 10-15 are illustrative, the cavity 1010 may include any count of accommodating cavities, and the component may be mounted at any position and have any size and/or shape. For example, one of the first accommodating cavity 1012-1 and the second accommodating cavity 1012-2 may be omitted. The cavity 1010 may include only one accommodating cavity. As another example, a shape of the cross section of the bore 1011 may be (substantially) a regular polygon or a circle. The regular polygon may be approximately a circle, which may make full use of space between an outer wall and the inner wall of the drum 1020 such that the drum 1020 may provide more space for arranging other components of the medical device 1000. Furthermore, the regular polygon or circular cross section may reduce the risk of collision between the couch top 1060 and the inner wall of the cavity 1010 when the drum 1020 rotates, which may improve the use (e.g., the patient) experience.

Moreover, FIGS. 10-15 and the above description thereof merely provide examples of the accommodating cavity 1012 configured to accommodate the couch top 1060. It should be noted that the accommodating cavity 1012 may be configured to accommodate other components or apparatus. For example, the accommodating cavity 1012 may also be configured to accommodate a support portion (e.g., the support portion 232-1 illustrated in FIG. 2) configured to support the couch top 1060. In such cases, a movement range of the couch top 1060 may also be increased.

Figure 16:
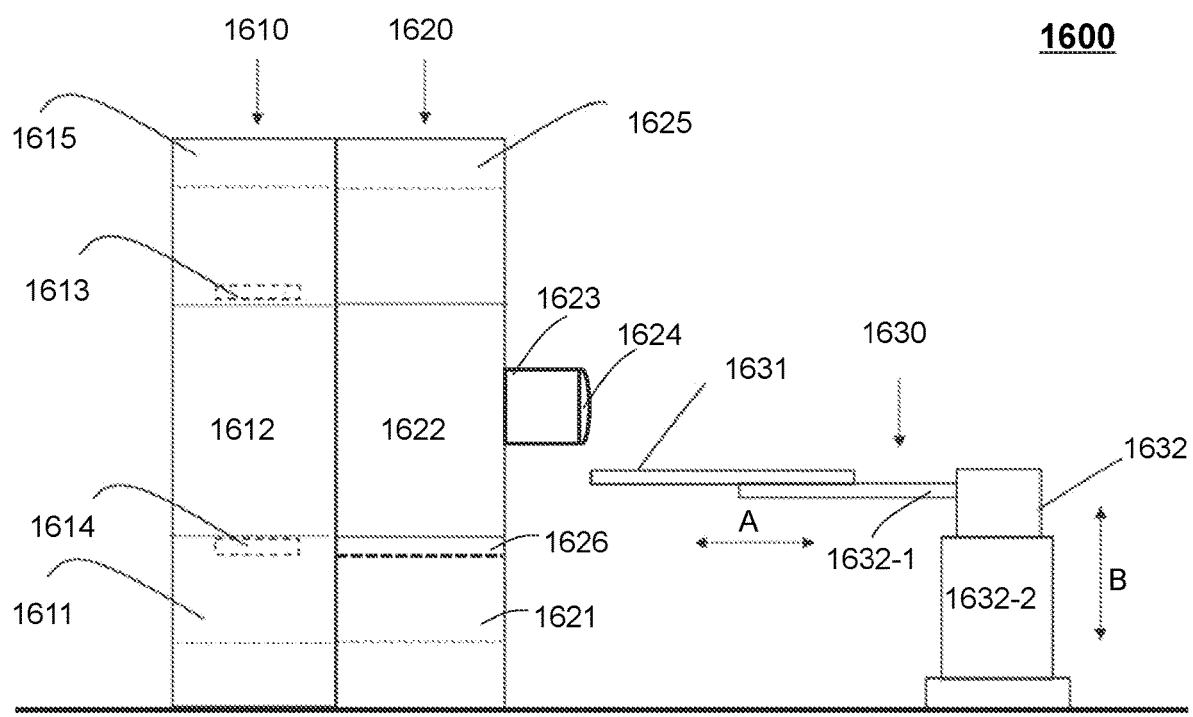
FIG. 16 is a schematic diagram illustrating an exemplary medical system according to some embodiments of the present disclosure.

FIG. 16 is a schematic diagram illustrating an exemplary medical system according to some embodiments of the present disclosure. As illustrated in FIG. 16, the medical system 1600 may include a first medical device 1610, a second medical device 1620, and a couch 1630. The first medical device 1610 and/or the second medical device 1620 may be an exemplary embodiment of the medical device 110 as described in connection with FIG. 1 or the medical device including the cavity 600 as described in connection with FIG. 6A.

In some embodiments, the first medical device 1610 may include an imaging device. As illustrated in FIG. 16, the first medical device 1610 may include a drum 1611 that defines a first bore 1612, a ray tube 1613, a detector 1614, and a housing 1615. In some embodiments, the first medical device 1610 may be an imaging device same as or similar to the imaging device 220 as described in connection with FIG. 2, which is not repeated herein.

In some embodiments, the second medical device 1620 may include a radiation therapy device. In some embodiments, the first medical device 1610 and the second medical device 1620 may be integrally formed. In some embodiments, the first medical device 1610 and the second medical device 1620 may be used separately, sequentially, or simultaneously. For example, the first medical device 1610 may acquire images while the second medical device 1620 is delivering radiation therapy. As illustrated in FIG. 16, the second medical device 1620 may include a drum 1621, a second bore 1622, a treatment arm 1623, a treatment head 1624, a housing 1625, and an accommodating cavity 1626. In some embodiments, the second medical device 1620 may also include an electronic portal imaging device (not shown).

In some embodiments, as illustrated in FIG. 16, the second medical device 1620 may be disposed between the first medical device 1610 and the couch 1630. The first bore 1612 of the first medical device 1610 and the second bore 1622 of the second medical device 1620 may be coaxial and connected with each other. The couch 1630 may include a couch top 1631 configured to move into or out of the first bore 1612 and the second bore 1622 along an axial direction of the first bore 1612 and the second bore 1622. The axial direction of the first bore 1612 and the second bore 1622 may be parallel to the horizontal direction A. The accommodating cavity 1626 may be disposed on an inner wall of the second bore 1622 and extends from an entrance of the second bore 1622 along the axial direction. In some embodiments, a length of the accommodating cavity 1626 may be less than a length of the second bore 1622 in the axial direction. As illustrated in FIG. 16, the accommodating cavity 1626 may form, with the second bore 1622, a connected space. In some embodiments, the accommodating cavity 1626 may be configured to provide an accommodating space for at least a portion of the couch 1630 in the radial direction of the second bore 1622.

In some embodiments, the couch may further include a support component 1632. The support component 1632 may include a support portion 1632-1 and a pedestal 1632-2. The support portion 1632-1 may be configured to support the couch top 1631. The pedestal 1632-2 may be configured to support the support portion 1632-1. In some embodiments, the accommodating cavity 1626 may be configured to accommodate the support portion 1632-1 to allow the support portion 1632-1 to move in the second bore 1622 along the axial direction. In such cases, a movement range of the couch top 1631 in the first bore 1612 may be increased. Merely by way of example, when treating a patient with a breast tumor, a breast bracket may be used to lift the upper body of the patient to facilitate treatment. Before the treatment, the patient may be imaged by the first medical device 1610 to determine a target region to be treated. Since the upper body of the patient is lifted, a position of the breast tumor may be higher than an isocenter plane of the first medical device 1610. In the imaging procedure, the couch top 1631 may be lowered to position the patient. For example, the couch top 1631 may descend in the first bore 1612 to move to a relatively low position such that the breast tumor may be positioned at the isocenter plane of the first medical device 1610. If the second medical device 1620 does not include the accommodating cavity 1626, the couch top 1631 may stop descending in the first bore 1612 when the support portion 1632-1 is in contact with an inner wall of the second bore 1622, which may limit the movement range of the couch top 1631. While in the second medical device 1620 with the accommodating cavity 1626, the support portion 1632-1 may be accommodated by the accommodating cavity 1626 such that the couch top 1631 may descend to a lowest point at which the couch top 1631 may be in contact with an inner wall of the first bore 1612. In such cases, the movement range of the couch top 1631 in the first medical device 1610 may be increased, which may reduce the difficulty of adjusting the position of the patient during an imaging procedure, thereby improving the accuracy of imaging and/or treatment of the target region of the subject and further improving the treatment efficiency.

In the medical system 1600, the accommodating cavity 1626 may be disposed in the second bore 1622 of the second medical device 1620, and the first bore 1612 of the first medical device 1610 may retain a conventional circular shape. The accommodating cavity 1626 may provide a space for accommodating at least a portion of the support portion 1632-1, which may facilitate the positioning of the patient in the first medical device 1610, thereby improving the treatment efficiency. Moreover, the support portion 1632-1 may move into the second bore 1622 to move the couch top 1631 into the first bore 1612. In such cases, the couch top 1631 may not need to be disposed with a long length, which may prevent sinking of the couch top 1631 caused by the length, thereby reducing a weight and occupied space of the medical system 1600.

The accommodating cavity according to some embodiments of the present disclosure, e.g., the accommodating cavity 620 as illustrated in FIG. 6A, the accommodating cavity 712 as illustrated in FIGS. 7-9, the accommodating cavity 712 as illustrated in FIGS. 10-15, and the accommodating cavity 1626 as illustrated in FIG. 16, provides an expansion of the bore in a bottom portion of the bore (e.g., the bore 610 in FIG. 6, the bore 711 in FIGS. 7-9, the bore 1011 in FIGS. 10-15) and/or in a top portion of the bore. It is understood that this is for illustration purposes and not intended to limit the scope of the present disclosure. The accommodating cavity may be arranged in one or more other portions of the bore to provide an expansion of the space of the bore, which in turn may allow more room to accommodate and/or maneuver a couch top or another component in the medical device. Merely by way of example, one or more accommodating cavities may be configured along the center line of the bore (e.g., the center line L of the bore 711 as illustrated in FIG. 7). As another example, the count or number of accommodating cavities configured in a bore may be one, two, three, four, five, etc.

It should be noted that the example illustrated in FIG. 16 and the above description thereof are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, a position of the first medical device 1610 relative to the second medical device 1620 and/or the couch 1630 may be variable. For example, the first medical device 1610 and the second medical device 1620 may be separate devices sharing the couch 1630. The couch 1630 may be located between the first medical device 1610 and the second medical device 1620. As another example, the first medical device 1610 and the second medical device 1620 may be separate devices located in different treatment rooms and use different couches. In some embodiments, the count, the position, the shape, and/or the size of the accommodating cavity may also be variable. For example, the accommodating cavity may also be disposed in the first medical device 1610.

It should be noted that the example illustrated in FIG. 16 and the above description thereof are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction performing system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A cavity of a medical device, comprising:
    a bore; and
    an accommodating cavity configured to provide an accommodating space for at least a portion of a couch in a radial direction of the bore, wherein
        the accommodating cavity is disposed on an inner wall of the bore and extends along an axial direction of the bore, and
        the accommodating cavity is configured to form, with the bore, a connected space in which the at least a portion of the couch is allowed to move along at least one of a first direction or a second direction in the connected space, wherein an included angle between the first direction and the second direction is larger than 0.

2. The cavity of claim 1, wherein a length of the accommodating cavity is less than a length of the bore in the axial direction.

3. The cavity of claim 1, wherein the accommodating cavity extends from an entrance of the bore.

4. The cavity of claim 1, wherein the accommodating cavity is configured to accommodate a couch top of the couch, a width of the accommodating cavity being larger than a width of the couch top.

5. The cavity of claim 4, wherein the couch includes a support portion configured to support the couch top, and the accommodating cavity is configured to accommodate the support portion, a width of the accommodating cavity being larger than a width of the support portion.

6. The cavity of claim 1, wherein the accommodating cavity is configured to accommodate the at least a portion of the couch in a vertical direction.

7. The cavity of claim 1, wherein a cross section of the cavity is of a shape other than a circle.

8. The cavity of claim 7, wherein the cross section of the cavity is polygonal.

9. The cavity of claim 7, wherein a movement range of the at least a portion of the couch in the first direction is larger than a movement range of the at least a portion of the couch in the second direction, the first direction and the second direction being radial directions of the bore.

10. The cavity of claim 9, wherein the first direction is a vertical direction.

11. The cavity of claim 10, wherein a distance between a center line of the bore in the axial direction and an upper inner wall of the cavity is less than a distance between the center line and a lower inner wall of the cavity.

12. The cavity of claim 1, further comprising:
    an adjustment assembly including a raised configuration and a retracted configuration, wherein when the adjustment assembly is at the retracted configuration, a distance between the adjustment assembly and an opening of the accommodating cavity is larger than 0.

13. The cavity of claim 12, wherein the adjustment assembly includes a cover configured to cover the opening of the accommodating cavity when the adjustment assembly is at the raised configuration.

14. The cavity of claim 12, further comprising:
    a control assembly configured to control the adjustment assembly to switch between the raised configuration and the retracted configuration.

15. The cavity of claim 1, further comprising a second accommodating cavity, wherein the second accommodating cavity is configured to form, with the bore and the accommodating cavity, the connected space.

16. A system, comprising:
    a first medical device and a second medical device, wherein a first bore of the first medical device and a second bore of the second medical device are coaxial and connected with each other; and
    a couch including a couch top configured to move into or out of the first bore and the second bore along an axial direction, wherein
        the first medical device or the second medical device includes an accommodating cavity that forms, with the first bore or the second bore, a connected space, wherein the accommodating cavity is configured to provide an accommodating space for at least a portion of the couch in a radial direction of the first bore or the second bore, and the at least a portion of the couch is allowed to move along at least one of a first direction or a second direction in the connected space, an included angle between the first direction and the second direction being larger than 0.

17. The system of claim 16, wherein
    the second medical device is disposed between the first medical device and the couch; and
    the second medical device includes the accommodating cavity.

18. The system of claim 17, wherein
    the accommodating cavity is disposed on an inner wall of the second bore and extends from an entrance of the second bore along the axial direction, a length of the accommodating cavity being less than a length of the second bore in the axial direction.

19. The system of claim 18, wherein the accommodating cavity is configured to accommodate a support portion of the couch that is configured to support the couch top to allow the support portion to move in at least one of the first bore or the second bore along the axial direction.

20. The system of claim 16, wherein the first medical device includes an imaging device, and the second medical device includes a radiation therapy device.

* * * * *